United States Patent
Hickle et al.

(10) Patent No.: US 7,152,604 B2
(45) Date of Patent: Dec. 26, 2006

(54) APPARATUS AND METHOD FOR MASK FREE DELIVERY OF AN INSPIRED GAS MIXTURE AND GAS SAMPLING

(75) Inventors: Randall S. Hickle, Lubbock, TX (US); Samsun Lampotang, Gainsville, FL (US)

(73) Assignee: Scott Laboratories, Inc., Lubbock, TX (US)

( * ) Notice: Subject to any disclaimer, the term of this patent is extended or adjusted under 35 U.S.C. 154(b) by 123 days.

(21) Appl. No.: 09/878,922

(22) Filed: Jun. 13, 2001

(65) Prior Publication Data

US 2002/0017300 A1 Feb. 14, 2002

Related U.S. Application Data

(63) Continuation-in-part of application No. 09/592,943, filed on Jun. 13, 2000, now Pat. No. 6,938,619.

(51) Int. Cl.
*A61M 16/00* (2006.01)

(52) U.S. Cl. ............ 128/207.14; 128/204.18; 128/204.22

(58) Field of Classification Search ......... 128/207.18, 128/116.26, 204.18, 204.22, 205.11
See application file for complete search history.

(56) References Cited

U.S. PATENT DOCUMENTS

| | | | |
|---|---|---|---|
| 4,141,353 A | 2/1979 | Dahlback et al. | 128/142 R |
| 4,151,843 A | 5/1979 | Brekke et al. | 128/203 |
| 4,263,908 A * | 4/1981 | Mizerak | 128/205.25 |
| 4,550,726 A | 11/1985 | McEwen | 128/202.22 |
| 4,602,644 A * | 7/1986 | DiBenedetto et al. | 600/538 |
| 4,612,928 A | 9/1986 | Tiep et al. | 128/204.23 |
| 4,618,099 A | 10/1986 | Nagao et al. | 239/332 |
| 4,686,974 A | 8/1987 | Sato et al. | 128/204.23 |
| 4,686,975 A | 8/1987 | Naimon et al. | 128/204.23 |

(Continued)

FOREIGN PATENT DOCUMENTS

EP 0 903 160 A1 3/1999

(Continued)

OTHER PUBLICATIONS

Oridion; 3.0 510(K) Summary Of Safety And Effectiveness Information; Oridion Medical Ltd.

*Primary Examiner*—Anhtuan T. Nguyen
*Assistant Examiner*—Darwin P Erezo
(74) *Attorney, Agent, or Firm*—Hogan & Hartson LLP

(57) ABSTRACT

Disclosed is an apparatus and method for the delivery of inspired gas, e.g., supplemental $O_2$, to a person combined with gas sampling, including for the purpose of monitoring of the ventilation of the person. In the invention, the delivery of inspired gas and gas sampling are accomplished without the use of a sealed face mask. The apparatus of one embodiment of the present invention comprises an oxygen delivery device, nasal airway pressure sampling devices, optionally an oral airway pressure sampling device and at least one pressure analyzer connected to the sampling devices which determine the phase of the person's respiration cycle and the person's primary airway. The oxygen delivery device is connected to a controller such that it delivers a higher flow of oxygen to the person during the inhalation phase of the person s respiratory cycle. The invention thus increases end tidal oxygen concentrations. The invention further comprises carbon dioxide sampling tubes that continuously sample gas from two nasal sites and the mouth. The nasal sampling tubes are connected to a switching valve that is in turn connected to a capnometer which determines carbon dioxide concentration during exhalation. The oral gas sampling site is connected to a second capnometer.

113 Claims, 13 Drawing Sheets

U.S. PATENT DOCUMENTS

| | | | | |
|---|---|---|---|---|
| 4,728,110 A | | 3/1988 | Nakasone | 277/213 |
| 4,858,476 A | * | 8/1989 | Tobin | 73/863.23 |
| 4,924,876 A | | 5/1990 | Cameron | 128/725 |
| 5,003,985 A | | 4/1991 | White et al. | 128/716 |
| 5,046,491 A | * | 9/1991 | Derrick | 128/200.24 |
| 5,050,614 A | | 9/1991 | Logan | 128/716 |
| 5,050,615 A | | 9/1991 | Malkamaki | 128/719 |
| 5,099,834 A | * | 3/1992 | Fishman | 128/203.12 |
| 5,099,836 A | | 3/1992 | Rowland et al. | 128/204.23 |
| 5,253,640 A | | 10/1993 | Falb et al. | 128/200.24 |
| 5,365,922 A | | 11/1994 | Raemer | 128/204.23 |
| 5,386,833 A | | 2/1995 | Uhen | 128/719 |
| 5,474,060 A | | 12/1995 | Evans | 128/204.22 |
| 5,485,850 A | | 1/1996 | Dietz | 128/716 |
| 5,535,739 A | * | 7/1996 | Rapoport et al. | 128/204.23 |
| 5,622,164 A | | 4/1997 | Kilis et al. | 128/200.24 |
| 5,626,131 A | * | 5/1997 | Chua et al. | 128/204.23 |
| 5,800,361 A | | 9/1998 | Rayburn | 600/532 |
| 5,865,174 A | | 2/1999 | Kloeppel | 128/204.23 |
| 5,937,858 A | * | 8/1999 | Connell | 128/207.14 |
| 6,017,315 A | | 1/2000 | Starr et al. | 600/538 |
| 6,155,986 A | | 12/2000 | Brydon et al. | 600/538 |
| 6,186,142 B1 | | 2/2001 | Schmidt et al. | 128/204.23 |
| 6,192,884 B1 | | 2/2001 | Vann et al. | 128/204.26 |
| 6,213,955 B1 | | 4/2001 | Karakasoglu et al. | 600/529 |
| 6,247,470 B1 | * | 6/2001 | Ketchedjian | 128/200.28 |
| 6,379,312 B1 | * | 4/2002 | O'Toole | 600/529 |
| 6,422,240 B1 | * | 7/2002 | Levitsky et al. | 128/207.18 |
| 6,439,234 B1 | * | 8/2002 | Curti et al. | 128/207.18 |
| 6,467,477 B1 | * | 10/2002 | Frank et al. | 128/203.23 |

FOREIGN PATENT DOCUMENTS

| | | |
|---|---|---|
| EP | 0 933 094 A2 | 4/1999 |
| WO | WO 90/04425 | 5/1990 |

\* cited by examiner

APPARATUS AND METHOD FOR MASK FREE DELIVERY OF AN INSPIRED GAS MIXTURE AND GAS SAMPLING

CROSS-REFERENCE TO RELATED APPLICATION

This application is a continuation-in-part of U.S. patent application Ser. No. 09/592,943 filed Jun. 13, 2000, the contents of which are incorporated herein.

BACKGROUND OF THE INVENTION

1. Field of the Invention

The invention relates to an apparatus and method for the delivery of an inspired gas (e.g., supplemental oxygen ($O_2$) gas) to a person combined with sampling of the gas exhaled by the person, such sampling for use, for example, in monitoring the ventilation of the person or for inferring the concentration of a drug or gas in the person's blood stream. More particularly, the invention relates to an apparatus and method where such delivery of the inspired gas and gas sampling are accomplished without the use of a sealed face mask.

2. Description of Related Art

In various medical procedures and treatments performed on patients, there is a need to deliver a desired inspired gas composition, e.g., supplemental oxygen, to the patient. In procedures involving the delivery of anesthesia or where a patient is otherwise unconscious and ventilated, the delivery of oxygen and gaseous or vaporized or nebulized drugs is typically accomplished via a mask that fits over the patient's nose and mouth and is sealed thereto or by a tracheal tube. In other procedures, however, for example, where a patient may be sedated, but conscious and breathing on their own, the delivery of supplemental oxygen or inspired gas may be accomplished via a mask or by nasal cannulae (tubes placed up each nare of a patient's nose), connected to a supply of oxygen or the desired gas composition.

Taking oxygen as one example of an inspired gas to be delivered to a person, the primary goal of oxygen supplementation (whether mask-free or otherwise) is to enrich the oxygen concentration of the alveolar gas, namely, the mixture of gas in the alveoli (microscopically tiny clusters of air-filled sacs) in the lungs. In a person with normal lung function, the level of oxygen in the deepest portion of the alveolar sacs is essentially reflected at the end of each "tidal volume" of exhaled gas (the volume of gas in one complete exhalation). The gas sample measured at the end of a person's exhalation is called the "end-tidal" gas sample.

So, for example, if a person breathes room air, room air contains 21% oxygen. When the person exhales, the end tidal gas will have about 15% oxygen; the capillary blood has thus removed 6% of the oxygen from the inhaled gas in the alveoli, to be burned by the body in the process of metabolism. Again, a simple goal of any form of oxygen supplementation is to increase the concentration of oxygen in the alveolar sacs. A convenient method of directly measuring or sampling the gas in alveolar sacs is by continuously sampling the exhaled gas at the mouth or nose and identifying the concentration of oxygen at the end-tidal point, a value that is reasonably reflective of the oxygen concentration in the alveolar sacs. Thus, one can compare the effectiveness of oxygen delivery systems by the amount that they increase the end tidal oxygen concentration.

If a person breathes through a sealing face mask attached to one-way valves and inhales a supply of 100% oxygen, the end tidal concentration of oxygen goes up to 90%. More specifically, once inert nitrogen gas has been eliminated from the lungs (after pure oxygen has been breathed for several minutes), alveolar gas will contain about 4% water vapor and 5% carbon dioxide. The remainder (about 90%) will be oxygen. Thus, the best oxygen delivery systems typically increase end tidal oxygen from a baseline of 15%, when breathing non-supplemented room air, to 90% when breathing pure oxygen. Although sealed face-masks are relatively effective oxygen delivery systems, conscious patients, even when sedated, often find masks significantly uncomfortable; masks inhibit the ability of a patient to speak and cause anxiety in some patients.

Nasal cannulae, on the other hand, do not typically cause the level of discomfort or anxiety in conscious patients that masks do, and thus, from a patient comfort standpoint, are preferable over masks for the delivery of oxygen to conscious patients. Nasal cannulae are, however, significantly less effective oxygen delivery systems than sealed face masks. Nasal cannulae generally increase the end tidal oxygen concentration to about 40% (as compared to 90% for a sealed mask). Nasal cannulae are less effective for at least two reasons.

First, when a person inhales, they frequently breathe through both nasal passages and the mouth (three orifices). Thus, the weighed average concentration of inhaled oxygen is substantially diluted to the extent of mouth breathing because 21% times the volume of air breathed through the mouth "weights down the weighted average."

Second, even if a person breathes only through their nose, the rate of inhalation significantly exceeds the supply rate of the nasal cannula (typically 2–5 liters/min.) so the person still dilutes the inhaled oxygen with a supply of 21% $O_2$ room air. If the nasal cannula is flowing at 2 liters per minute and a person is inhaling a liter of air over 2 seconds, the inhalation rate is 30 liters per minute, and thus, most of the inhaled volume is not coming from the nasal cannula, but rather from the room. Increasing the oxygen flow rate does not effectively solve this problem. First, patients generally find increased flow very uncomfortable. Second, increased inspired gas flow dilutes (washes away) exhaled gases like carbon dioxide and/or exhaled vapors of intravenous anesthetics or other drugs. When this happens carbon dioxide cannot be accurately sampled as a measure of respiratory sufficiency. Also, a drug such as an inhalational or intravenous anesthetic, cannot be accurately sampled as a measure of the arterial concentration of the drug from which, for example, the level of sedation might be inferred. There is a need in various medical procedures and treatments to monitor patient physiological conditions such as patient ventilation (the movement of gas into and out of the lungs, typically measured as a volume of gas per minute). If the patient does not move air into and out of the lungs then the patient will develop oxygen deficiency (hypoxia), which if severe and progressive is a lethal condition. Noninvasive monitoring of hypoxia is now available via pulse oximetry. However, pulse oximetry may be late to diagnose an impending problem because once the condition of low blood oxygen is detected, the problem already exists. Hypoventilation is frequently the cause of hypoxemia. When this is the case, hypoventilation can precede hypoxemia by several minutes. A good monitor of ventilation should be able to keep a patient "out of trouble" (if the condition of hypoventilation is diagnosed early and corrected) whereas a pulse oximeter often only diagnoses that a patient is now "in" trouble. This pulse oximetry delay compared to ventilatory monitoring is especially important in acute settings where respiratory depressant drugs are administered to the patient, as is usually the case during painful procedures performed under conscious sedation.

Ventilatory monitoring is typically measured in terms of the total volumetric flow into and out of a patient's lungs. One method of effective ventilatory monitoring is to count respiratory rate and then to measure one of the primary effects of ventilation (removing carbon dioxide from the body). Certain methods of monitoring ventilation measure the "effect" of ventilation (pressure oscillations, gas flow, breath sound and exhaled humidity, heat or $CO_2$ at the airway). Other ventilation methods measure the "effort" of ventilation (e.g., transthoracic impedance plethysmography, chest belts, respiratory rate extraction from optoplethysmograms). Effort-based ventilation monitors may be less desirable because they may fail to detect a blocked airway where the patient generates the effort (chest expansion, shifts in blood volume, etc.) but does not achieve the desired effects that accompany gas exchange.

There are a variety of ventilation monitors such as 1) airway flowmeters and 2) capnometers (carbon dioxide analyzers). These monitors are used routinely for patients undergoing general anesthesia. These types of monitors work well when the patient's airway is "closed" in an airway system such as when the patient has a sealing face mask or has the airway sealed with a tracheal tube placed into the lungs. However, these systems work less well with an "open" airway such as when nasal cannulae are applied for oxygen supplementation. Thus, when a patient has a non-sealed airway, the options for tidal volume monitoring are limited. With an open airway, there have been attempts to monitor ventilation using capnometry, impedance plethysmography, humidity, heat, sound and respiratory rate derived from the pulse oximeter's plethysmogram. Some of the limitations are discussed below.

Nasal capnometry is the technique of placing a sampling tube into one of the nostrils and continuously analyzing the carbon dioxide content present in the gas stream thereof. Nasal capnometry is relatively effective provided that 1) the patient always breathes through his/her nose, and 2) nasal oxygen is not applied. More specifically, if the patient is talking, most of the exhalation is via the mouth, and frequent false positive alarms sound because the capnometer interprets the absence of carbon dioxide in the nose as apnea, when in fact, it is merely evidence of talking. Some devices in the prior art have tried to overcome this problem by: manual control of sampling from the nose or mouth (Nazorcap); supplementing oxygen outside of the nose while sampling for $CO_2$ up inside the nose (BCI); providing oxygen in the nose while sampling $CO_2$ from the mouth (BCI); and supplying oxygen up one nostril and sampling for $CO_2$ up inside the other nostril (Salter Labs). None of these already-existing systems provide oxygen to both the nose and mouth or allow automatic control of sampling from either site or account for the possibility that one nostril may be completely or partially obstructed compared to the other one. Further, if nasal oxygen is applied to the patient, the carbon dioxide in each exhalation can be diluted significantly by the oxygen supply. In this case, the capnometer may interpret the diluted $CO_2$ sample as apnea (stoppage in breathing), resulting once again, in frequent false positive alarms. Dilution of $CO_2$ may also mask hypoventilation (detected by high $CO_2$) by making a high $CO_2$ value appear artifactually normal and thus lull the clinician into a false sense of security, that all is well with the patient.

Impedance plethysmography and plethysmogram respiratory rate counting also suffer drawbacks as primary respiratory monitors. Both devices measure the "effort" of the patient (chest expansion, shifts in blood volume). Impedance plethysmography is done via the application of a small voltage across two ECG electrode pads placed on each side of the thoracic cage. In theory, each respiration could be detected as the phasic change of thoracic impedance. Unfortunately, the resulting signal often has too much noise/artifact which can adversely affect reliability. Respiratory rate derived from the pulse oximeter's plethysmogram may not diagnose apnea and distinguish it from complete airway obstruction, thus misdiagnosing apnea as a normal condition (a false negative alarm state).

The arterial concentration of an inhalational or intravenous drug or gas is clinically useful and may be inferred from the end-tidal concentration of the drug or gas measured in the gases exhaled by the patient. The end-tidal concentration of a desired component of the exhaled gas mixture can be monitored and used to infer the arterial concentration. Examples of drugs and gases that can be monitored include, among other things: propofol, xenon, intravenous anesthetics and sedatives, and water vapor.

Various inspired gas compositions may be administered to patients for different purposes. Oxygen diluted with air may be used instead of pure $O_2$ to reduce the risk of an oxygen-enriched micro-environment that may support or promote ignition of a fire, especially for those procedures using lasers (such as laser resurfacing of the face). An oxygen-helium mixture may be used to reduce the resistance to flow. An oxygen/air/bronchodilator mixture may be used to treat bronchoconstriction, bronchospasm or chronic obstructive pulmonary disease (COPD). A mixture of $O_2$ and water vapor may be used to humidify and loosen pulmonary secretions.

In view of the above drawbacks to current systems for delivering inspired gas and gas sampling, including monitoring ventilation, there is a need for an improved combined system to accomplish these functions.

SUMMARY OF THE INVENTION

One of the purposes of the current invention is to increase the alveolar concentration of an inspired gas, such as oxygen, without the requirement for a patient to wear a face mask. This is done by, among other things: a) determining the patient's breath phase, namely whether the person is in the inhalation or exhalation phase of their respiratory cycle; and b) delivering a higher flow of inspired gas during the inhalation part of the respiratory cycle thereby making this higher flow of inspired gas acceptable to patients. In one aspect of the invention the inspired gas flow may be provided to all three respiratory orifices (i.e., both nostrils and the mouth) or directly in front of the mouth, during the inhalation cycle. Thus, dilution of inhaled gas by room air at an inhalation portal is reduced.

A second purpose of the invention is to more effectively sample exhaled gases, such sampling could be used, for example, to monitor patient ventilation, in combination with mask-free delivery of inspired gas to the patient. In this aspect, the invention includes placing pressure lumens and gas-sampling lumens inside, or near, at least one of a patient's nostrils and, in some embodiments, the mouth. The pressure lumens are connected to pressure transducers that in turn are connected to a controller or processor running custom software algorithms for determining breath phase (inhalation or exhalation) and rate. The pressure samples from the respective lumens are compared with one another to determine the primary ventilatory path. The gas sampling tubes may be connected to gas analyzers or monitors, e.g., $CO_2$ analyzers, that measure the level of a gas or drug in the exhaled gas.

Other aspects of the invention will be apparent from the description below.

DESCRIPTION OF PREFERRED EMBODIMENTS

Single Capnometer Embodiment

The concept of the invention will now be described using, merely by way of example, supplemental oxygen as the inspired gas mixture and gas sampling of carbon dioxide in the patient's exhalations. It should be understood that the concept of the invention is not limited to supplemental $O_2$ administration and $CO_2$ sampling.

Figure 1:
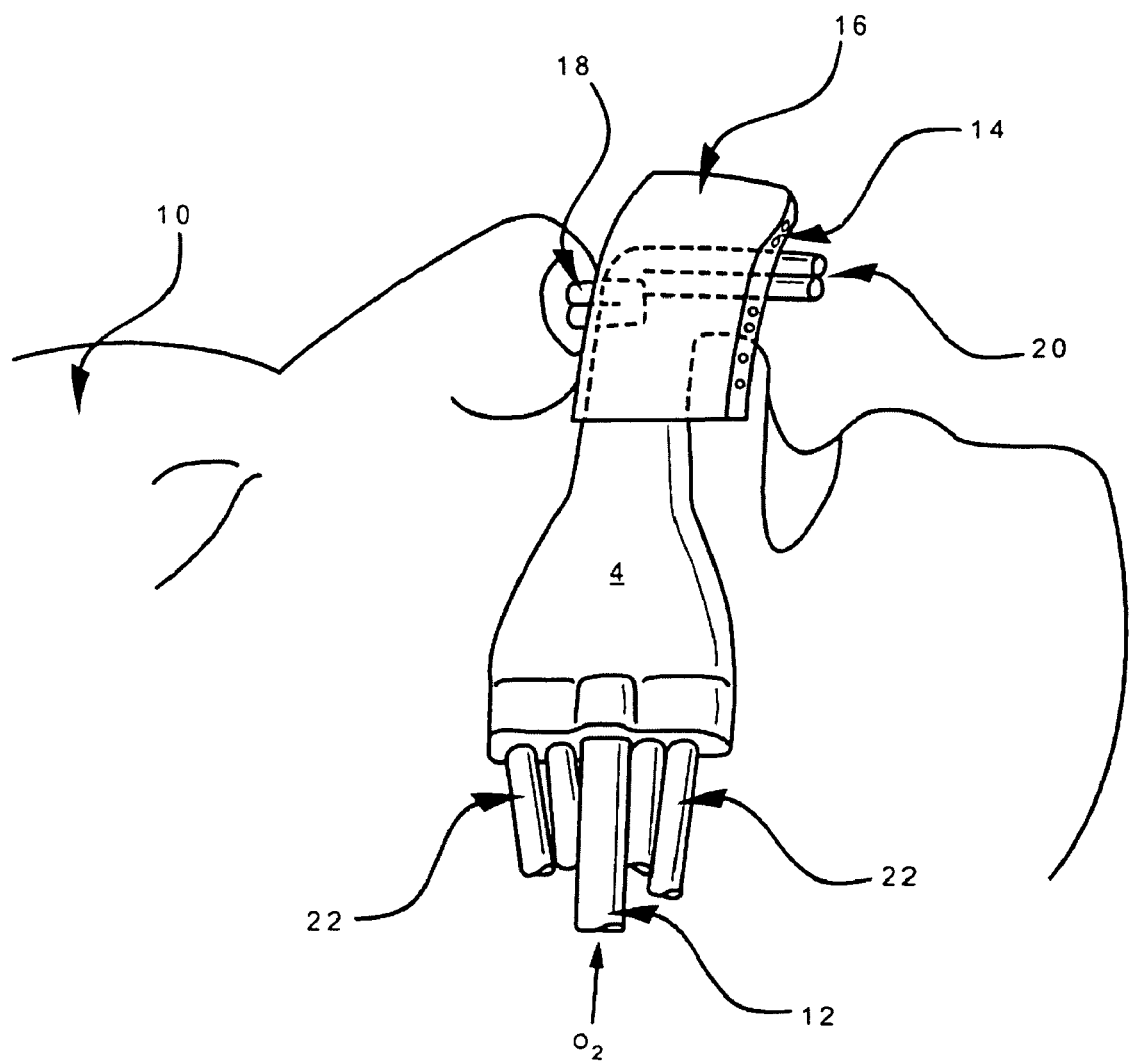
FIG. 1 shows a side, cut out view of the disposable portion of the apparatus placed on a patient in accordance with one embodiment of the invention.

FIG. 1 shows a cut-out view of the disposable portion 4 of an apparatus in accordance with the invention placed on a patient 10.

The apparatus provides for the mask-free delivery of supplemental oxygen gas to the patient combined with the monitoring of patient ventilation. Oxygen gas is supplied to the patient from an $O_2$ supply tube 12 and exits portion 4 from a diffuser grid 14 in housing 16 (shown in more detail in FIG. 2). Diffuser grid 14 blows diffused oxygen into the immediate area of the patient's nose and mouth. Two thin lumens (tubes) are mounted adjacent one another to portion 4 and placed in one of the patient's nostrils (nasal lumens 18). Another two thin lumens are also mounted adjacent to one another to portion 4 and placed in front of the patient's mouth (oral lumens 20).

Of nasal lumens 18, one lumen is a pressure lumen for sampling the pressure resulting from a patient's nose breathing and the other lumen continuously samples the respiratory gases so they may be analyzed in a capnometer to determine the concentration of carbon dioxide. This arrangement is essentially the same for oral lumens 20, namely, one lumen is a pressure lumen (samples pressure in mouth breathing) and the other lumen continuously samples the respiratory gases involved in mouth breathing.

Nasal lumens 18 and oral lumens 20 are each connected to their own pneumatic tubes, e.g., 22, which feed back the nasal and oral pressure samples to pressure transducers (not shown) and which feed back the nasal and oral gas samples to a capnometer (not shown). All of portion 4; lumens 18, 20; oxygen supply tubing 12 and feedback tubing 22 are disposable (designed to be discarded, e.g., after every patient use), and preferably constructed of pliable plastic material such as extruded polyvinyl chloride.

Figure 2:
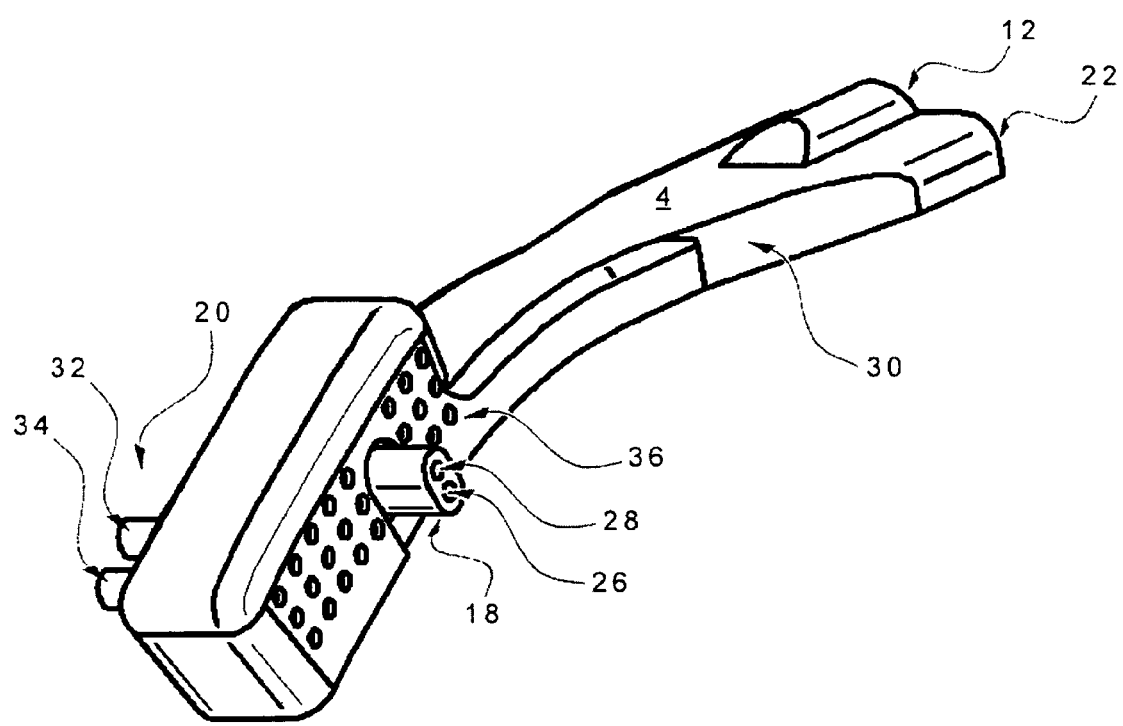
FIG. 2 shows a perspective exterior view of the disposable portion of the apparatus in accordance with one embodiment of the invention.

As shown in FIG. 2, lumens 18, 20 and tubings 12 and 22, although shown as a portion cut-out in FIG. 1 in a preferred embodiment, are housed in cover 30. Also, in FIG. 2, nasal lumens 18 (including pressure lumen 28 and gas sampling lumen 26) are preferably formed from a double-holed, single-barrel piece. Oral lumens 20 (which include pressure lumen 32 and gas sampling lumen 34) are preferably formed from a double barrel piece. Diffuser grid 36 is formed in cover 30 and functions as an oxygen diffuser which releases a cloud of oxygen into the immediate oral and nasal area of the patient 10.

Figure 3:
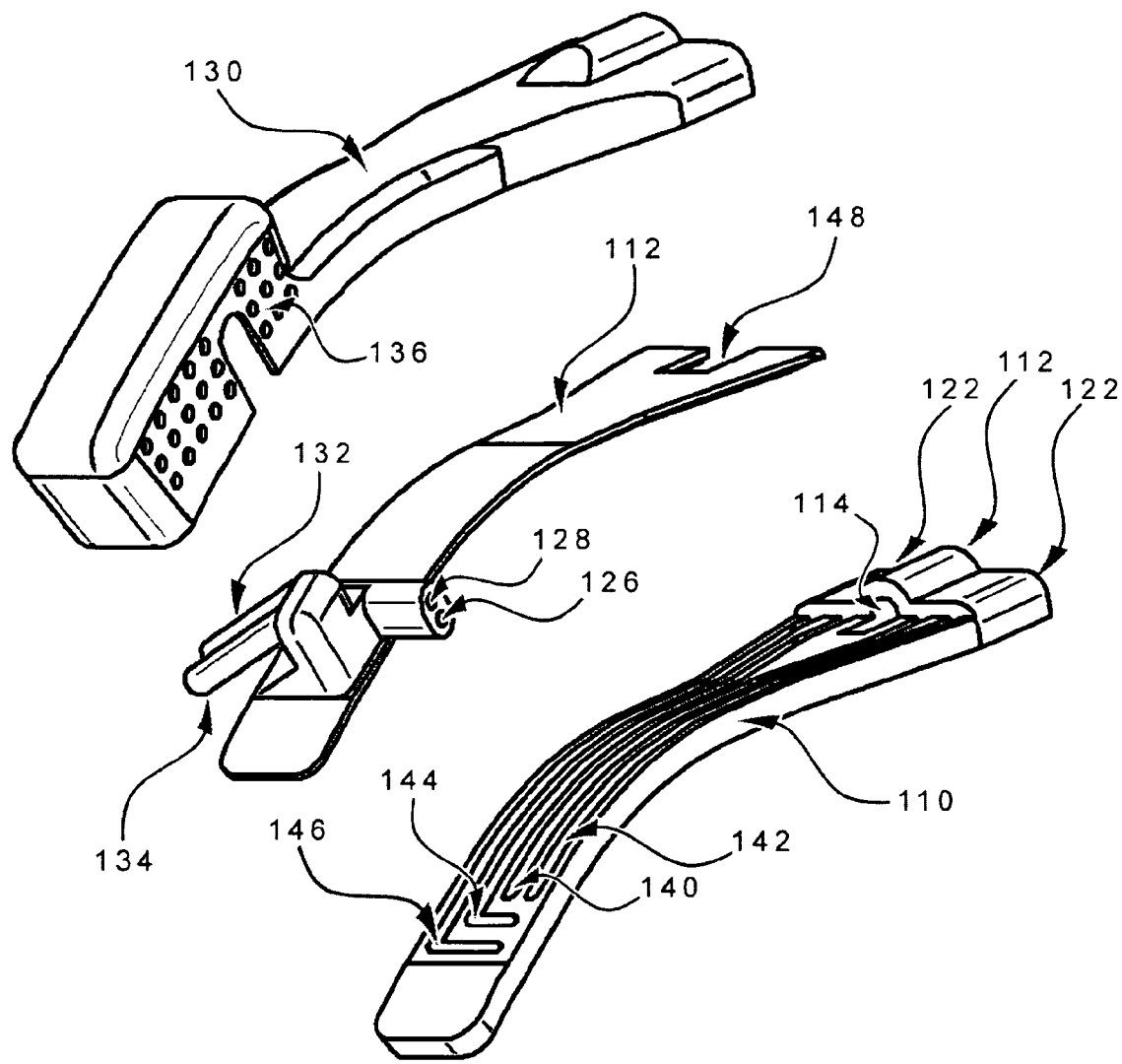
FIG. 3 is a blow-up view showing the lower, middle and cover portions of the disposable portion of the apparatus in accordance with one embodiment of the invention.

FIG. 3 shows disposable portion 4 including cover 30 in more detail in cut-out fashion. Specifically, lower portion 110, formed from a suitably firm, but not rigid, plastic, has an opening 112 for insertion of oxygen supply tube 12. Slot 114 in portion 110 receives the oxygen gas from the tube 12, retains it, and forces it up through opening 148 in middle portion 112. Middle portion 112 is affixed to lower portion 110 lying flat on portion 110. From opening 148, the oxygen gas travels into cover 130 (affixed directly onto middle portion 112) and travels lengthwise within cover 130 to the diffuser portion, whereupon the oxygen exits cover 130 through diffuser grid 136 into the immediate vicinity of the patient's nose and mouth in a cloud-like fashion. It is preferable to supply oxygen flow to all three respiratory orifices (both nostrils and mouth) to increase the concentration of oxygen provided to the patient. By providing flow to all three orifices, dilution of inhaled gas at an inhalation portal by pure room air is reduced. Also, a diffused stream such as that created by grid 136 is a preferred embodiment for the oxygen stream delivered to the patient. This is because a stream of oxygen delivered through a single lumen cannula is typically uncomfortable at the higher flow rates necessary for sufficient oxygen delivery. Further, at those flow rates, a single lumen can create an undesirable Bernoulli effect. It is noted that an alternative to the diffuser grid 136 is a cup-shaped or other chamber which receives the $O_2$ jet stream and includes a foam or filler paper section for diffusing the jet stream of $O_2$.

As is also shown in FIG. 3, feedback tubing 22 enters lower portion 110 at openings 122. At opening 122 begin grooves 146 and 140 formed in lower portion 110 each for receiving the feedback pressure sample from lumens 128 and 132. At opening 122 begin grooves 144 and 142, formed in lower portion 110 each for receiving the feedback $CO_2$ sample from lumens 126 and 134. Grooves 146, 144, 140 and 142, all formed in lower portion 110, connect at one end to their respective sampling lumens (128, 126, 132 and 134) and at their other end to feedback tubing 22; middle portion 112 lies flat on and affixed to portion 110 such that the grooves 146, 144, 140 and 142 form passageways for the respective feedback samples. As can be seen, when assembled, portions 130, 112 and 110 together form whole disposable piece 4, shown perspectively in FIG. 2.

Figure 4:
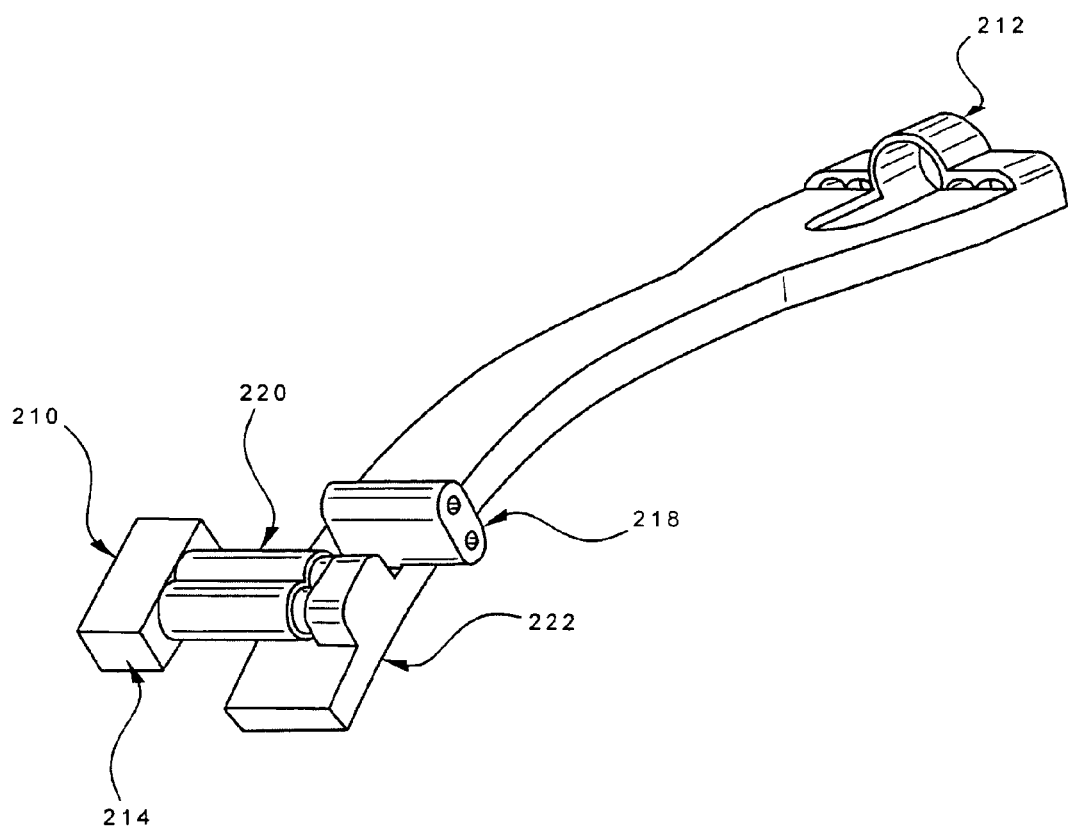
FIG. 4 shows an embodiment of the disposable portion of the apparatus with an oral collection chamber in accord with one embodiment of the invention.

FIG. 4 shows a preferred embodiment of disposable portion 4 (here portions 110 and 112 are shown affixed to one another) with an oral sample collection chamber 210 fitting over oral lumens 220 (nasal lumens are shown at 218 and the opening for the oxygen supply tube is shown at 212). Oral sample collector 210 is preferably constructed of plastic and creates a space in chamber 214 that collects a small volume of gas the patient has breathed orally. That volume of gas is then sampled by lumens 220 and fed back for analysis through the respective pressure and $CO_2$ feedback tubing to pressure transducers and the capnometer described above. Collector 210 thus acts as a storage container for better sampling of the oral site. It also serves as a capacitor for better monitoring of oral site pressure (exhalation contributes to volume and pressure increases, while inhalation removes gas molecules from volume 214 and pressure decreases).

In one preferred embodiment, collector 210 is provided in a variety of sizes and shapes to collect different volumes of air or to facilitate different medical procedures which may be performed in or near the mouth. In another preferred embodiment collector 210 is adjustable in that it is capable of sliding over lumens 220 to enable positioning directly over the mouth's gas stream. In a further embodiment, lumens 220 are themselves also slidably mounted to portion 222 so as to be extendable and retractable to enable positioning of both the lumens and collector directly in front of the oral gas stream.

The present invention generally provides that in the event that positive pressure ventilation has to be applied via face mask, it should be possible to leave the apparatus of the invention in place on the person to minimize user actions during an emergency. Thus, the apparatus of the invention allows a face mask to be placed over it without creating a significant leak in the pillow seal of the face mask. The material of the apparatus in contact with the face is preferably soft (e.g., plasticized PVC, etc.) and deformable. This prevents nerve injury, one of the most common complications of anesthesia, which is often caused by mechanical compression or hyperextension that restricts or shuts off the blood supply to nerves.

Figure 5A:
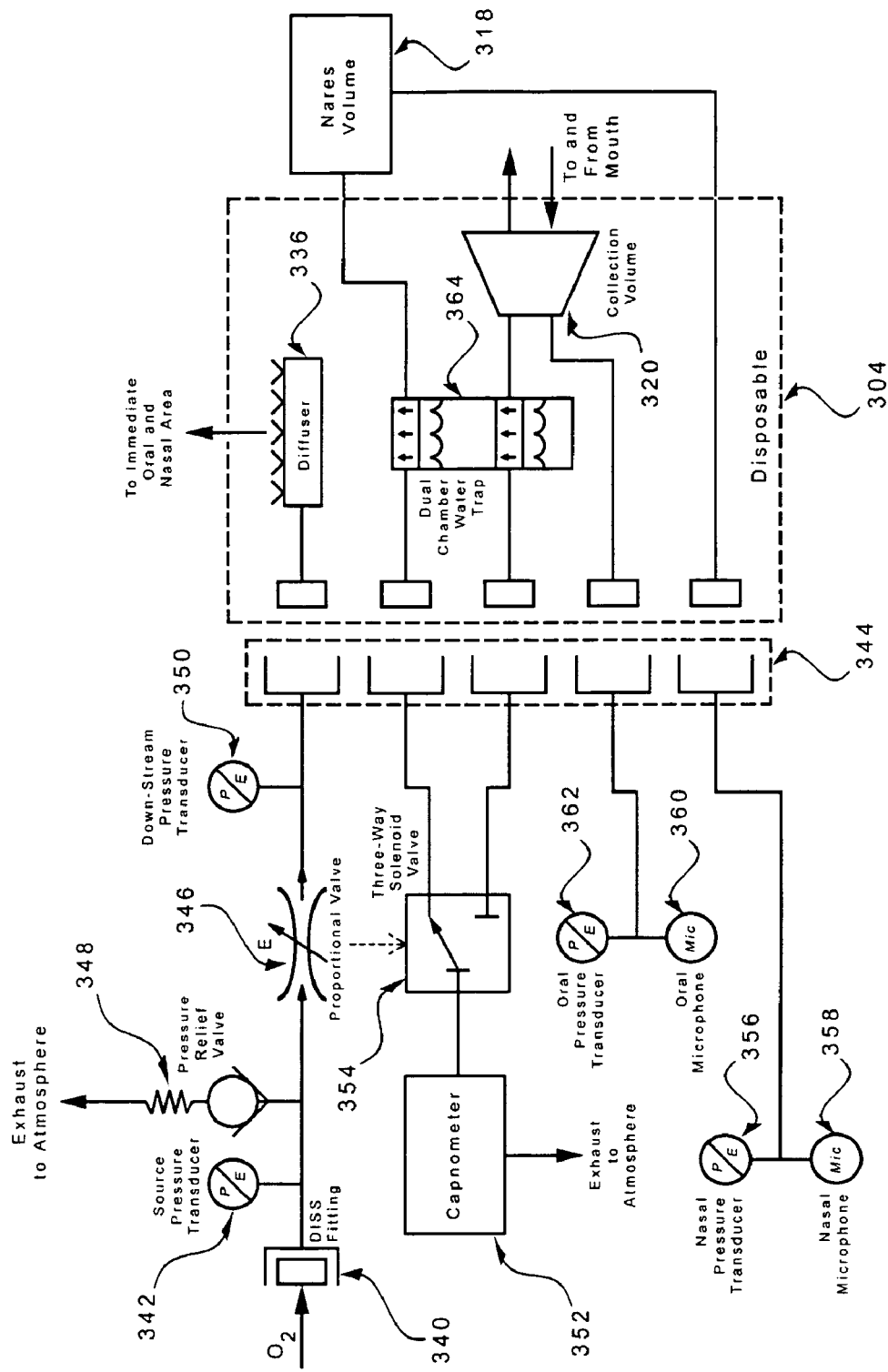
FIG. 5A is a schematic diagram of a gas delivery and gas sampling system in accordance with one embodiment of the invention.

FIG. 5A shows a schematic circuit diagram of a preferred embodiment of the oxygen delivery and gas sampling system of the invention. As described above, disposable portion 304 includes nasal lumens which sample a nasal (nares) volume 318 of gas breathed through the patient's nostril; an oral sample collector which creates an oral volume of gas 320 effecting sampling of gas breathed through a patient's mouth; and an oxygen diffuser 336 which enriches the immediate breathing area of a patient with oxygen, increasing the patient's fraction of inspired oxygen and thereby increasing the patient's alveolar oxygen levels. The diffuser 336 ensures that a high rate of oxygen flow is not uncomfortable for the patient.

Oxygen gas is supplied to diffuser 336 from an oxygen supply ($O_2$ tank or in-house oxygen). If the supply of $O_2$ is from an in-house wall source, DISS fitting 340 is employed. The DISS fitting 340 (male body adaptor) has a diameter indexed to only accept a Compressed Gas Association standard oxygen female nut and nipple fitting. A source pressure transducer 342 monitors the oxygen source pressure and allows custom software running on a processor (not shown) to adjust the analog input signal sent to proportional valve 346 in order to maintain a user-selected flow rate as source pressure fluctuates. Pressure relief valve 348 relieves pressure to the atmosphere if the source pressure exceeds 75 psig. Proportional valve 346 sets the flow rate of oxygen (e.g., 2.0 to 15.0 liters per minute) through an analog signal and associated driver circuitry (such circuitry is essentially a voltage to current converter which takes the analog signal to a dictated current to be applied to the valve 346, essentially changing the input signal to the valve in proportion to the source pressure, as indicated above). It is noted that flowrates of 2.0 and 15.0 L/min could also be accomplished by 2 less expensive on/off valves coupled with calibrated flow orifices instead of one expensive proportional flow control valve. Downstream pressure transducer 350 monitors the functionality of proportional valve 346. Associated software running on a processor (not shown) indicates an error in the delivery system if source pressure is present, the valve is activated, but no downstream pressure is sensed. As described above, the nares volume 318 and oral collection volume 320 are fed back to the capnometer 352 via a three-way valve 354. The capnometer 352 receives the patient airway gas sample and monitors the $CO_2$ content within the gas sample. Software associated with capnometer 352 displays pertinent parameters (such as a continuous carbon dioxide graphic display known as a capnogram and digital values for end-tidal $CO_2$ and respiration rate) to the user. A suitable capnometer may be that manufactured by Nihon Kohden (Sj5i2) or CardioPulmonary Technologies ($CO_2$WFA OEM). Three-way valve 354 automatically switches the sample site between the oral site and the nasal site depending on which site the patient is primarily breathing through. This method is described in more detail below, but briefly, associated software running on a processor (not shown) switches the sample site based on logic that determines if the patient is breathing through the nose or mouth. It is preferable to have a short distance between the capnometer and valve 354 to minimize dead space involved with switching gas sample sites.

Also as described above, the nares volume 318 collected is fed back to a nasal pressure transducer 356 and nasal microphone 358. Transducer 356 (such as a Honeywell DCXL01DN, for example) monitors the pressure in the nares volume 318 through the small bore tubing described above. Associated software running on a processor (not shown) determines through transducer 356 if the patient is breathing primarily through the nose. Associated offset, gain and temperature compensation circuitry (described below) ensures signal quality. Nasal microphone 358 monitors the patient's breath sounds detected at the nasal sample site. Associated software allows the user to project sound to the room and control audio volume. Output from nasal microphone 358 may be summed with output of the oral microphone 360 for a total breath sound signal. In an additional embodiment the breath sound signals are displayed to the user and/or further processed and analyzed in monitoring the patient's physiological condition.

Oral pressure transducer 362 (such as a Honeywell DCXL01DN, for example) monitors pressure at the oral collection volume 320 through the small bore tubing described above. Associated software running on a processor (not shown) determines via pressure transducer 362 if the patient is primarily breathing through the mouth. Offset gain and temperature compensation circuitry ensure signal quality. Oral microphone 360 operates as nasal microphone 358 described above that amplifies and projects breath sounds to the room. Alternatively, a white noise generator reproduces a respiratory sound proportional to the amplitude of the respiratory pressure and encoded with a sound (WAV file) of a different character for inhalation versus exhalation so that they may be heard and distinguished by a care giver in the room.

A dual chamber water trap 364 guards against corruption of the $CO_2$ sensors by removing water from the sampled gases. Segregated chambers collect water removed by hydrophobic filters associated with the nasal and oral sites. This segregation ensures that the breathing site selected as the primary site is the only site sampled. The disposable element 304 is interfaced to the non-disposable elements via a single, multi-lumen connector 344 that establishes five flow channels in a single action, when it is snapped to the medical device containing the non-disposable equipment.

Figure 5B:
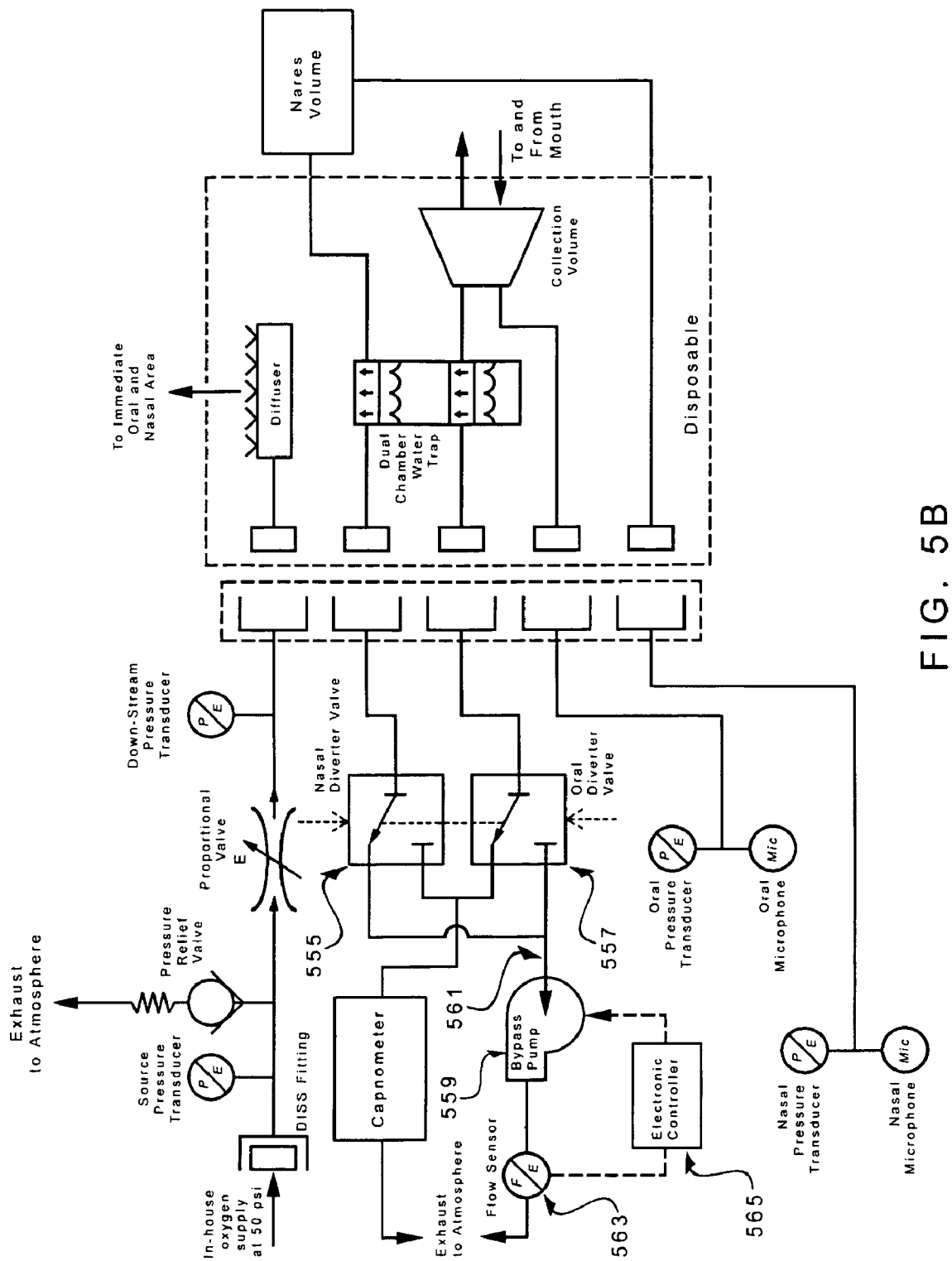
FIG. 5B is a schematic diagram of a gas delivery and gas sampling system in accordance with an alternative embodiment of the invention.

FIG. 5B shows an additional embodiment of the system circuit of the present invention, including a gas sample bypass circuit which keeps the gas sample at the oral and nasal sites flowing at the same rate, regardless of whether the site is being sampled by the capnometer or bypassed. Specifically, nasal diverter valve 555 switches the nasal gas sample site between the capnometer and the bypass line. Activation of the valve 555 is linked to activation of oral diverter valve 557 in order to ensure that one sample site is connected to the bypass line while the other sample site is connected to the capnometer. This allows two states: 1) the oral gas sample site fed back to the capnometer, with the nasal gas sample site connected to the bypass; and 2) the nasal gas sample site fed back to the capnometer with the oral gas sample site on bypass. As described above, the control software switches the gas sample site based on logic that determines if the patient is breathing through the nose or mouth. Oral diverter valve 557 switches the oral gas sample site between the capnometer and the bypass line and operates as described with respect to nasal diverter valve 555.

Bypass pump 559 maintains flow in the bypass line 561 that is equivalent to flow dictated by the capnometer (e.g., 200 cc/min.). The pump 559 also ensures that the gas sample sites are synchronized with one another so that the $CO_2$ waveform and respiration rate calculations are not corrupted when gas sample sites are switched. Flow sensor 563 measures the flow rate obtained through the bypass line 561 and provides same to electronic controller 565 necessary for flow control. Controller 565 controls the flow of pump 559.

As can be seen from FIG. 5B, balancing the flow between the active gas sample line and the bypass line (e.g., maintaining a flow in the bypass equivalent or near equivalent to the flow within the $CO_2$ sampling line, e.g., 200 cc/min) is desired. This prevents corruption of the $CO_2$ waveform and respiration rate calculations in the event one site became occluded such that the bypass and capnometer lines flowed at different rates.

Figure 6:
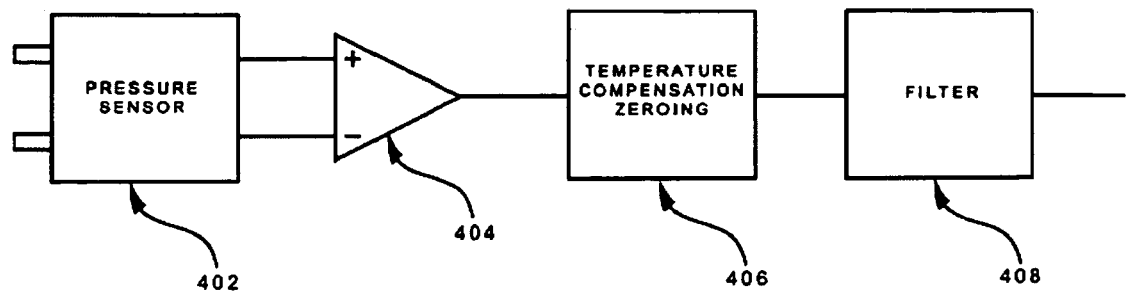
FIG. 6 is a schematic diagram of pressure transducer circuitry in one embodiment of the invention.

FIG. 6 shows a schematic of the electronic circuitry associated with pressure transducers 356 and 362. Such circuitry includes a pressure sensor 402, a hi-gain amplifier 404, a temperature compensation and zeroing circuit 406 and a low pass filter 408. The gain and temperature zeroing circuit ensure signal quality for the pressure transducer output. Depending on the signal to noise ratio of the pressure transducer 402, the low pass filter 408 may be optional.

Figure 7:
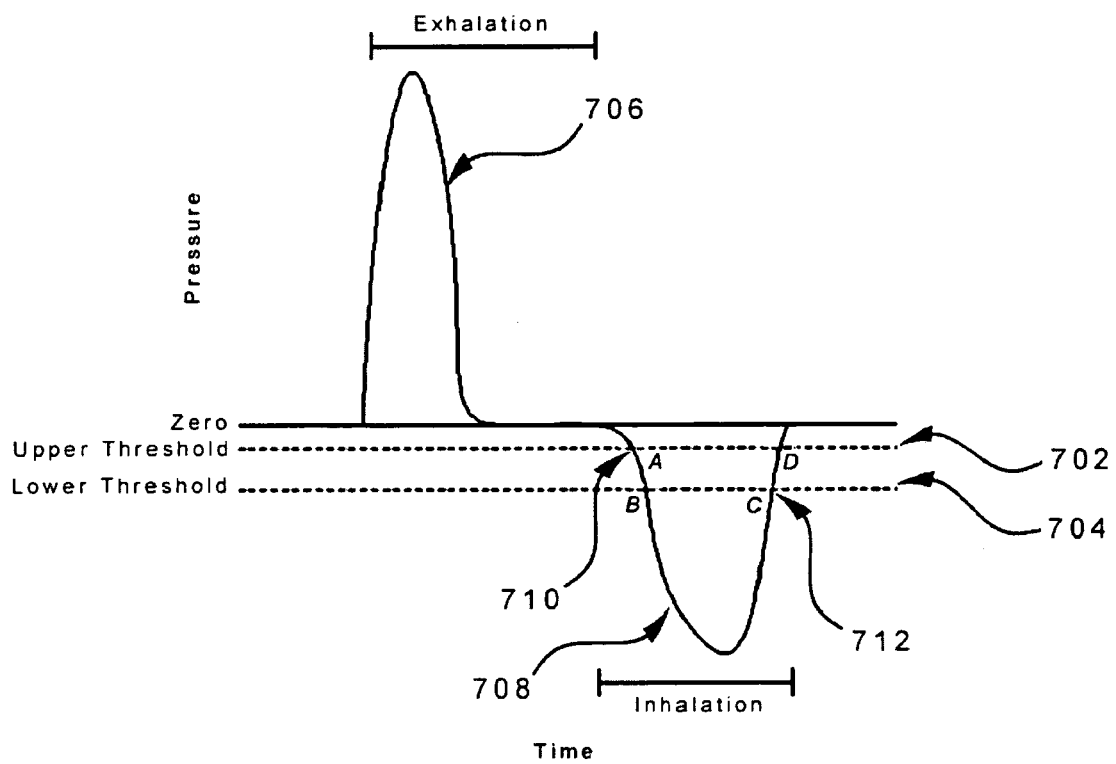
FIG. 7 is a diagram of a pressure waveform during a respiration cycle used in one method of the invention.

FIG. 7 is a diagram of the pressure reading (oral or nasal) during a typical respiration cycle with thresholds A, B, C and D identified in accordance with the preferred method of the invention. As is shown, as exhalation 706 begins, the pressure becomes positive, eventually reaching a peak then dropping back to zero (atmospheric pressure) as the exhalation completes. The beginning of inhalation 708 is indicated by the pressure becoming negative (sub-atmospheric). The pressure will become more negative during the first portion of inhalation then trend back towards zero as inhalation ends.

The control software of the present invention defines an upper and a lower threshold value 702, 704, respectively. Both are slightly below zero, with the lower threshold 704 being more negative than the upper threshold 702. During each respiration cycle the software determines when the thresholds 702, 704 are crossed (points A, B, C, and D, FIG. 7) by comparing the pressures to one of the two thresholds. The crossings are expected to occur in sequence, i.e., first A, then B followed by C, and finally D. An $O_2$ source valve is turned up (e.g., to 10–15 liters/min of flow) when point A, 710, is reached and turned down (e.g., to 2–3 liters/min of flow) when C, 712, is reached, thus providing the higher oxygen flow during the majority of the inhalation phase.

Figure 8:
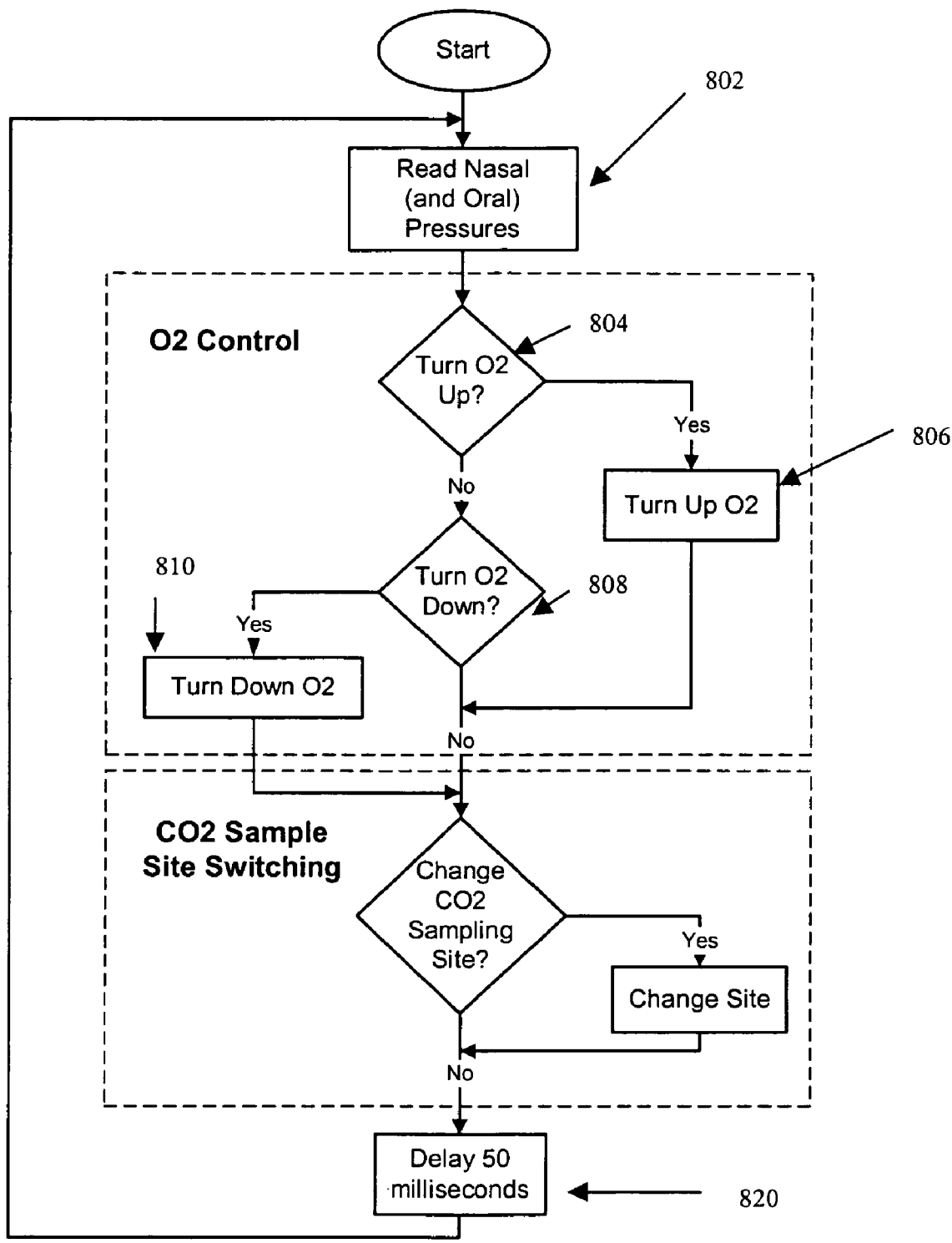
FIG. 8 is a flow chart of a preferred embodiment of one method of the invention.

To determine when the threshold crossings occur, the software examines the pressures from the oral and nasal pressure sensors at periodic intervals, e.g., at 50 milliseconds (see FIG. 8, step 820). During each examination, the software combines the oral and nasal pressures and then compares the combined pressure to one of the two thresholds as follows.

As shown by the flowchart of FIG. 8, when the software begins execution, it reads the nasal and oral pressures, step 802, and awaits a combined pressure value less than the upper threshold (point A), step 804. When this condition is met, the software turns up the $O_2$ valve, step 806, to a higher desired flow (e.g., 10–15 liters/min) then begins looking for a combined pressure value less than the lower threshold (point B), step 808. When this occurs the software waits for a combined pressure value that is greater than the lower threshold (point C). When this value is read, the $O_2$ is turned down to the lower desired flow rate (e.g., 2–3 liters/min), step 810, and the software awaits a pressure value that exceeds the upper threshold (point D). Once this value is read, the cycle begins again for the next breath. In the case of oxygen, the invention may thus increase end tidal oxygen concentrations from the baseline 15% (breathing room air) up to 50–55%. Whereas this may not be as effective as face mask oxygen supplementation, it is significantly better than the prior art for open airway oxygen supplementation devices.

Also, instead of completely shutting off inspired gas flow during exhalation, the invention selects a baseline lower flow of inspired gas, e.g., 2 L/min, so that the flow interferes minimally with the accuracy of exhaled gas sampling. The non-zero inspired gas flow during exhalation enriches the ambient air around the nose and mouth that is drawn into the lungs in the subsequent inhalation. Further, in the event that $O_2$ is the inspired gas and that the software malfunctions such that the algorithm stays stuck in the exhalation mode, a non-zero baseline flow of $O_2$ will ensure that the patient breathes partially $O_2$-enriched room air rather than only room air.

As described above, a capnometer may be used to provide information such as end-tidal $CO_2$ and respiration rate by continually sampling the level of $CO_2$ at a single site. Since breathing can occur through the nose, mouth, or both, the software must activate valve 354 (FIG. 5A) or valves 555 and 557 (FIG. 5B), that switch the capnometer-sampling site to the source providing the best sample, i.e., mouth or nose.

As is also shown in FIG. 8, the software determines the best sampling site by examining the oral and nasal pressure readings at periodic intervals. During each examination, the current and prior three oral pressure values are compared to the corresponding nasal pressure values. If the combined nasal pressures exceed the combined oral pressures by more than a factor of three, the capnometer sample is obtained at the nose. If the combined oral pressures exceed the combined nasal pressures by more than a factor of three, the sampling occurs at the mouth.

It is further noted that the gas sampling lumens may be connected together at a switching valve to minimize the number of gas analyzers required. Via the switching valve, the gas sampling lumen connected to the primary ventilatory path is routed to the gas analyzer. Additionally, in some aspects of the invention, the user sees a display from one gas analyzer. For example, for a capnometry application, the $CO_2$ tracing that has the highest averaged value (area under the curve over the last n seconds, e.g., 15 seconds) is displayed. Because the present invention measures the "effect," i.e., the $CO_2$ and airway pressure variations with each breath, it would not fail to detect a complete airway obstruction.

Multiple Capnometer Embodiment

Figure 9:
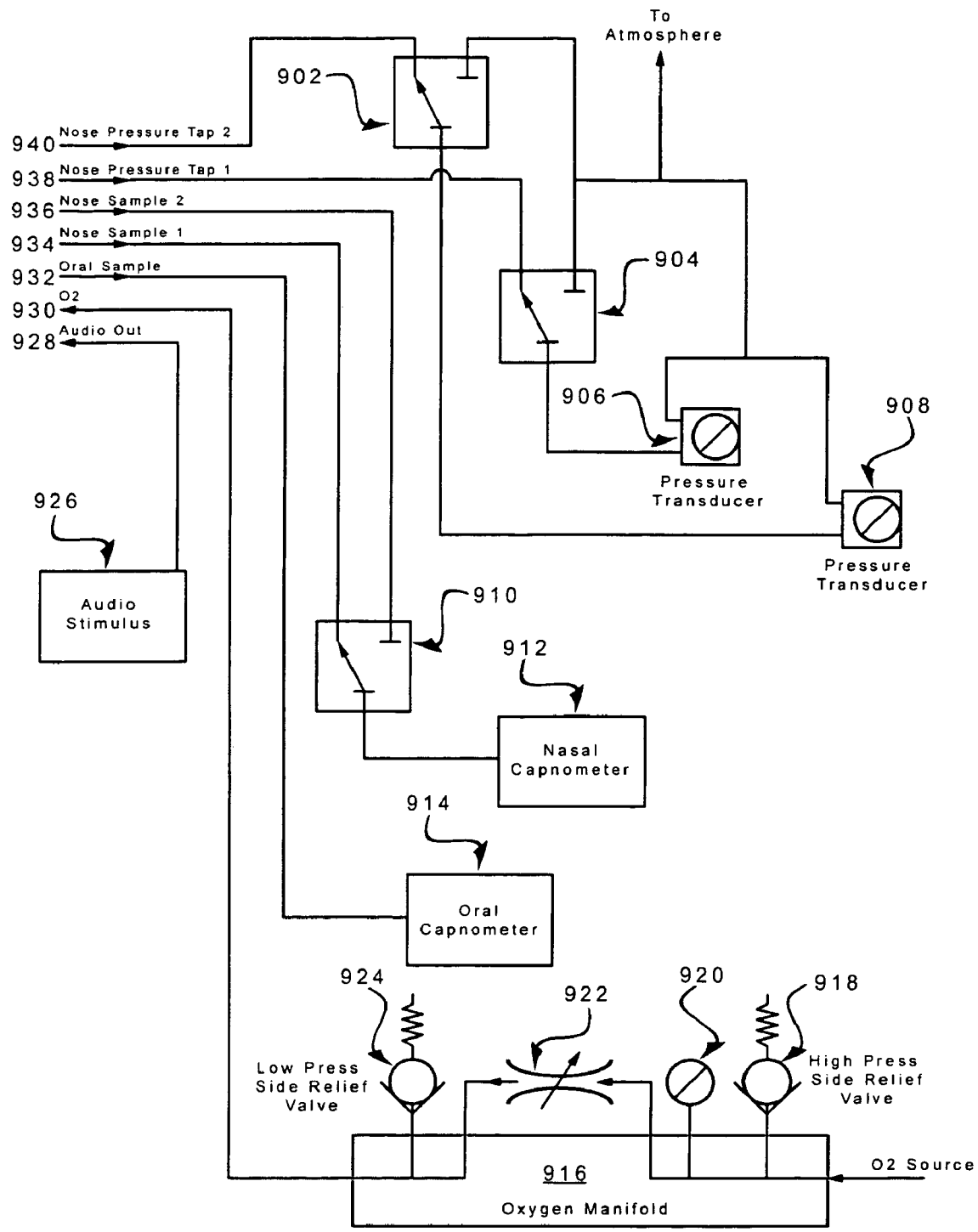
FIG. 9 is a schematic diagram of a gas delivery and gas sampling system in accordance with an alternative embodiment of the invention.

An alternative embodiment of the invention uses two capnometers as shown in FIG. 9, 912 and 914. Pressure transducer 906 monitors the pressure at nose tap 938. Pressure transducer 908 monitors the pressure at nose tap 940. Each nose tap 938 and 940 samples the pressure in one of the patient's nares. Pressure transducers 906 and 908 can be momentarily connected to atmosphere for zeroing purposes via valves 904 and 902 respectively. Pressure is not monitored at the mouth. The primary nasal ventilatory path is determined from analysis of the pressure trace at each nares. The nare whose pressure trace exhibits the larger amplitude of pressure oscillation is considered to be the primary nasal ventilatory path.

Gas sample lumens are placed at both nares and at the mouth. The oral gas sample lumen 932 is directly connected to the oral capnometer 914. The nasal capnometer 912 can be connected to either of the nasal gas sampling lumens 934 or 936 via a switching valve 910. Once the pressure transducers and the software determine the primary nasal ventilatory path, the switching valve routes the gas sample from the primary nasal ventilatory path to the nasal capnometer 912. Thus, exhaled gas is sampled continuously from either the right or left nasal passage.

The software analyzes the sum of the pressures sampled from the two nasal orifices to determine whether the patient is inhaling or exhaling. Obviously, different algorithms may be possible like determining the breath phase from only the pressure trace at the primary nasal ventilatory path, instead of adding the pressures from both nares. Software running on a processor (not shown) opens a valve 922 connected to an oxygen source so that oxygen flow is high (e.g., 15 L/min) during the inhalation phase of the patient's breathing. A high pressure relief valve 918 relieves pressure if the $O_2$ supply pressure exceeds 75 psig. A pressure transducer 920 monitors the $O_2$ supply pressure such that the software can adjust the opening of the valve 922 to compensate for $O_2$ supply pressure fluctuations. A pressure relief valve 924 downstream of the valve 922 prevents pressure buildup on the delivery side. Components 918, 920, 922 and 924 are mounted on a gas manifold 916 with internal flow passages (not shown) to minimize the number of pneumatic connections that have to be manually performed.

An audio stimulus generated by sub-system 926 is used to prompt the patient to perform a specific action like pressing a button as a means of assessing responsiveness to commands as an indirect measure of patient consciousness. This automated responsiveness test is useful in a conscious sedation system like, for example, that described in U.S. patent application Ser. No. 09/324,759 filed Jun. 3, 1999.

Figure 10:
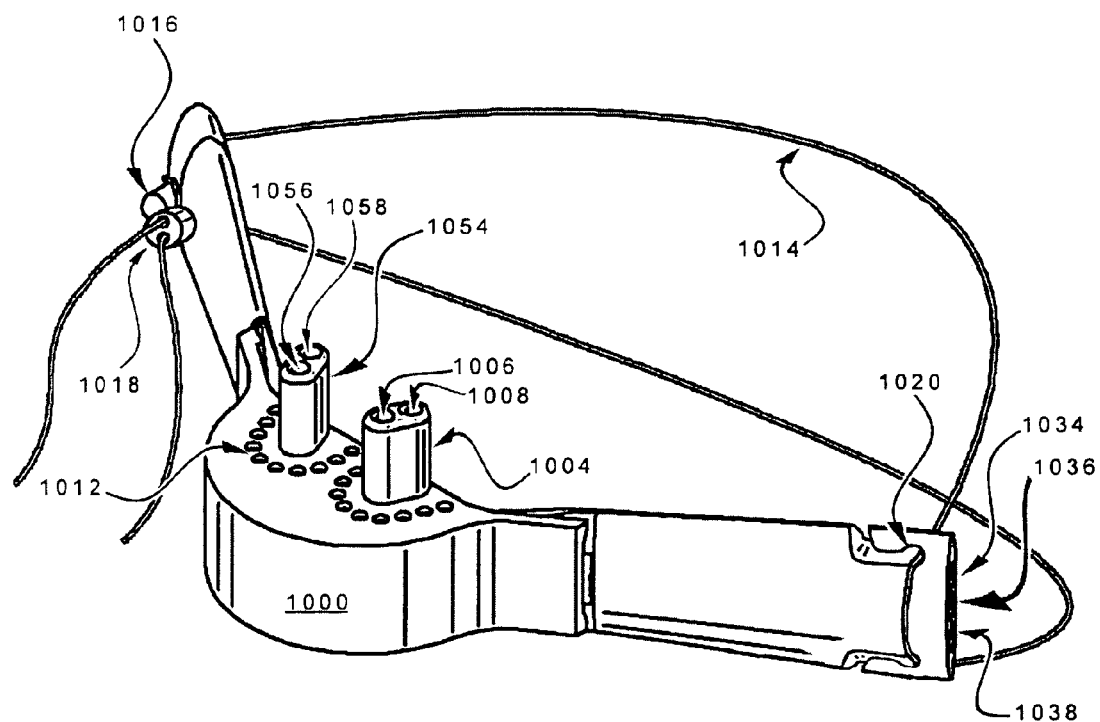
FIG. 10 is a perspective diagram of an alternative embodiment of an oronasal gas diffuser and gas sampling device in accord with the invention.

The oronasal piece 1000 in FIG. 10 is intended for use with the circuit in FIG. 9. A pressure sampling lumen 1008 and a gas sampling lumen 1006 are contained within left nostril insert 1004 that fits into the left nare of the patient. A pressure sampling lumen 1058 and a gas sampling lumen 1056 are contained within right nostril insert 1054 that fits into the right nare of the patient. A multiplicity of holes 1012 diffuse $O_2$ near the region of the nares. A similar multiplicity of holes 1026 (FIG. 12) diffuse $O_2$ near the region of the mouth, to account for the possibility of mouth breathing. The oronasal piece 1000 is held onto the patient's face via an adjustable loop of cord or elastic band 1014 that is designed to be rapidly adjusted to the patient. A single cord or elastic band is made to form a loop by passing both cut ends via an adjustment bead 1018. The loop is attached in one motion to bayonet-type notches 1020 on oronasal piece 1000 that securely hold the cord in place on the oronasal piece while it is being wrapped around the back of the patient's head. The adjustment bead 1018 is then slid along the loop to adjust the tension on the cord. Once adjusted, the loop is then released over the stud 1016 such that the stud tends to splay the two pieces of cord apart, thus locking the adjustment bead to prevent inadvertent loosening of the adjustment bead. The gas sample lumen 1024 (FIG. 11) is contained within protuberance 1022 which is designed to stick out into the stream of gas flowing to and from the mouth.

Figure 11:
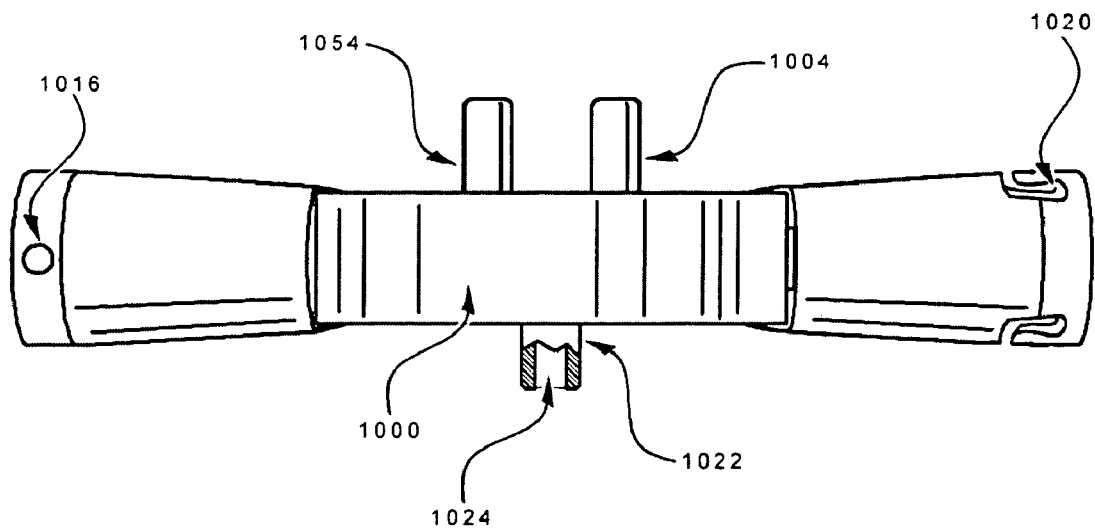
FIG. 11 is a side-elevation frontal view of the device shown in FIG. 10.
Figure 12:
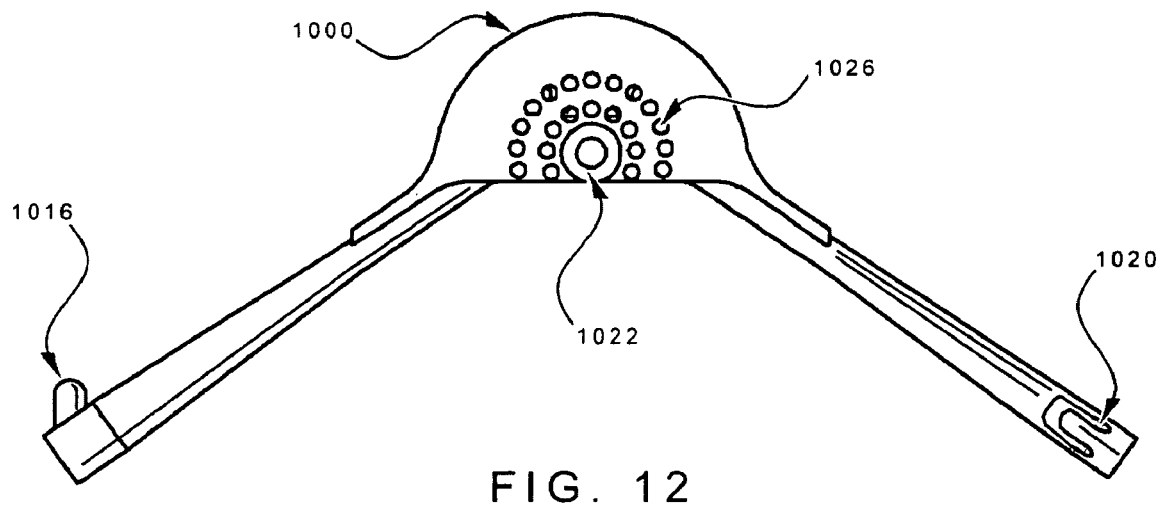
FIG. 12 is a plan view of the bottom of the device shown in FIG. 10.
Figure 13:
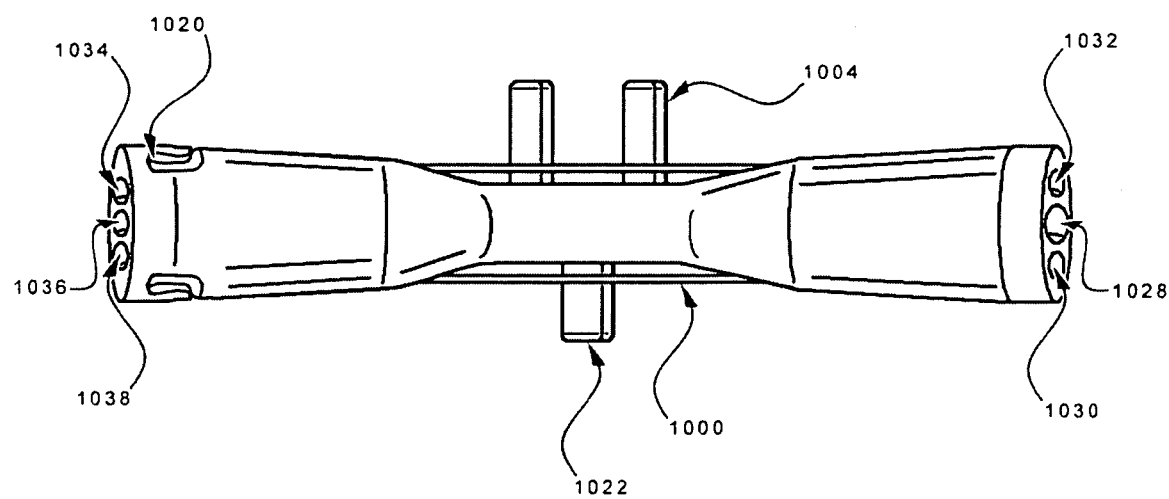
FIG. 13 is a side-elevation back view of the device shown in FIG. 10.

Referring now to FIG. 13, lumen 1038 on the oronasal piece 1000 is internally connected to the gas sample lumen 1006 (FIG. 10) for the left nare. Lumen 1036 (FIG. 13) on the oronasal piece 1000 is internally connected to the oral gas sample lumen 1024 (FIG. 11). Lumen 1034 (FIG. 13) on the oronasal piece 1000 is internally connected to the pressure sampling lumen 1008 (FIG. 10) for the left nare. Lumen 1030 (FIG. 13) on the oronasal piece 1000 is internally connected to the gas sample lumen 1056 (FIG. 10) for the right nare. Lumen 1028 (FIG. 13) on the oronasal piece 1000 is internally connected to the multiplicity of holes 1012 and 1026 (FIGS. 10 and 12) that allow $O_2$ to diffuse into the regions close to the nose and mouth. Lumen 1032 (FIG. 13) on the oronasal piece 1000 is internally connected to the pressure sampling lumen 1058 (FIG. 10) for the right nare. The details of the internal flow passages in oronasal piece 1000 to accomplish the above connections will be evident to one skilled in the art.

Figure 14:
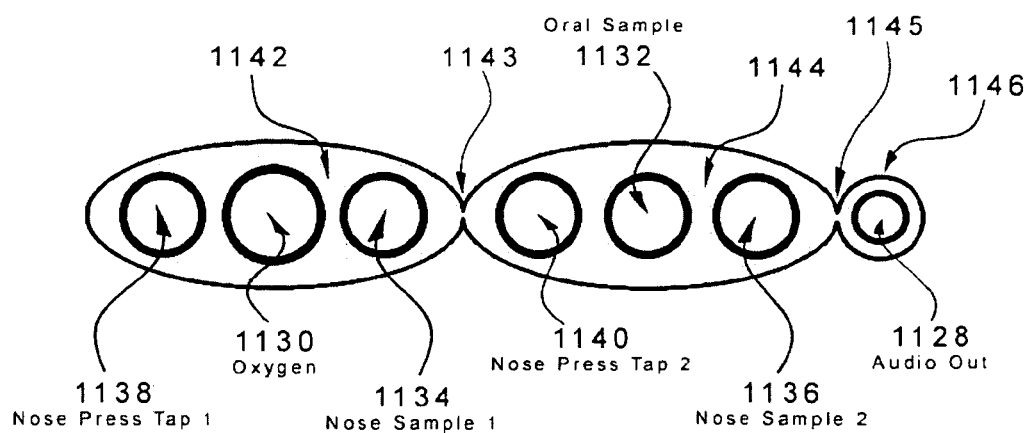
FIG. 14 is a cross-sectional view of the tubing that connects the device in FIG. 10 to the circuitry in FIG. 9.

Referring to FIG. 14, the oronasal piece 1000 of FIG. 10 is connected to the circuit of FIG. 9 via the extruded tear-apart tubing of FIG. 14. The extruded tubing contains seven lumens grouped in three clusters (1142, 1144 and 1146) that can be separated from each other by manually tearing along the tear lines 1143 and 1145. Lumen 1130 in cluster 1142 channels the flow of O₂ to the oronasal piece and is of larger bore to accommodate the high flow of O₂ and present minimal flow resistance. Lumen 1128 in cluster 1146 carries the audio stimulus that prompts the patient to squeeze a button as part of an automated responsiveness test (ART) system. Lumen 1132 in the middle of cluster 1144 carries the oral gas sample. Lumens 1138 and 1134 in cluster 1142 carry the pressure and gas samples from one nasal insert. Lumens 1140 and 1136 in cluster 1144 carry the pressure and gas samples from the other nasal insert. The cross-section of each cluster is shaped like an aerofoil to adapt to the indentation of the facemask pillow seal and the cheek of the patient when a facemask is placed over the separated clusters. The lumens are arranged such that the larger bore lumens are in the middle of each cluster, taking advantage of the aerofoil like cross-section of each cluster.

Figure 15:
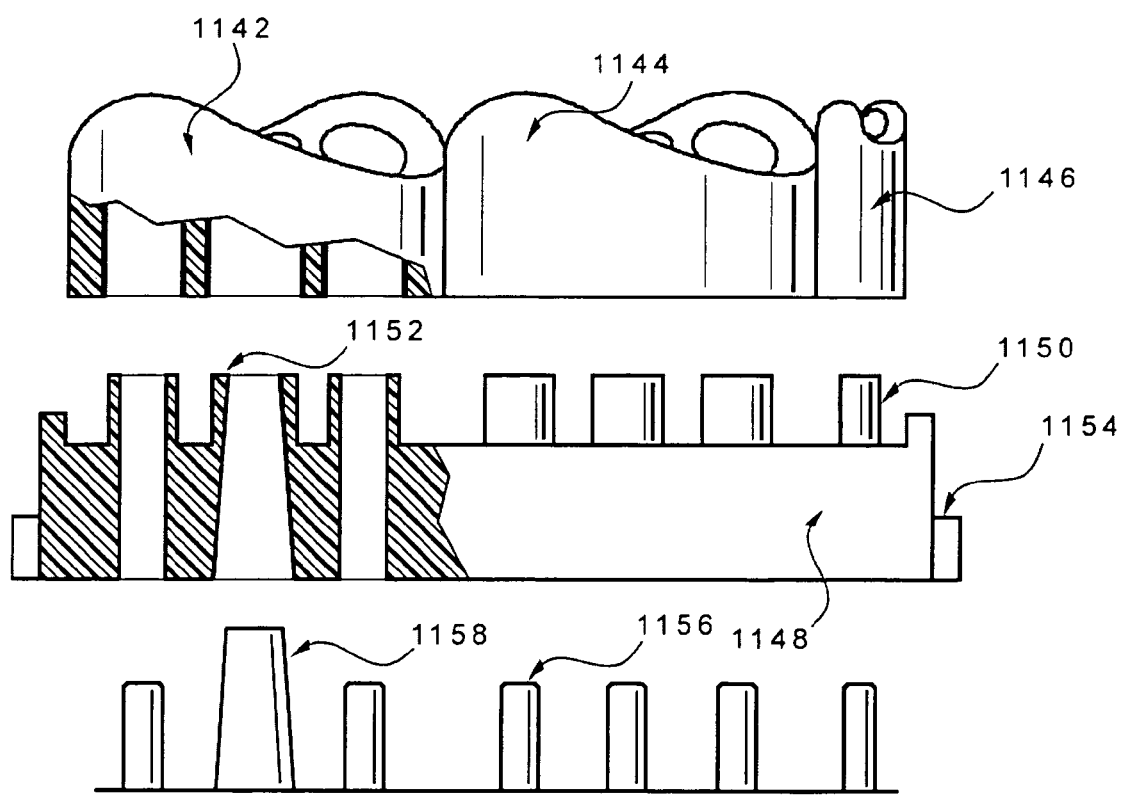
FIG. 15 is a view of a connector that interfaces the machine end of the extruded tubing of FIG. 14 to a medical device.

An additional feature of the invention is that the pneumatic harness (shown in cross-section in FIG. 14) can be connected to a standard, male, medical O₂ barbed outlet connector commonly referred to as a "Christmas tree," so that the oronasal piece of the invention can also be used post-procedurally to deliver O₂-enriched air to the patient. Another feature of the invention is that the pneumatic harness of FIG. 14 can be snapped onto a medical device with a single action. To accomplish both design objectives, the connector of FIG. 15 is used to adapt the pneumatic harness of FIG. 14 for connection to a medical device. The pneumatic harness of FIG. 14 is mounted onto adapter 1148 using seven male ports like ports 1150 and 1152. Port 1152 carries the oxygen inflow and port 1150 pipes in the audio stimulus. The adapter 1148 has a tapered inlet connected to the O₂ delivery lumen 1130 (FIG. 14). The tapered inlet is made of soft material and is designed to mate to a standard male O₂ barbed connector known as a Christmas tree. The connector snaps into a socket on the medical device to establish seven airtight pneumatic connections with only one action. Tapered male port 1158 on the medical device delivers oxygen into lumen 1130 via port 1152. Port 1156 brings in the pressure signal from nose pressure tap 2. Pegs 1154 allow the multi-lumen connector 1148 to be held in tightly and securely once snapped into the medical device to prevent accidental disconnection.

The above-described systems and methods thus provide improved delivery of inspired gas and gas sampling, including CO₂ sampling, without use of a face mask. The system and method may be particularly useful in medical environments where patients are conscious (thus comfort is a real factor) yet may be acutely ill, such as in hospital laboratories undergoing painful medical procedures, but also in the ICU, CCU, in ambulances or at home for patient-controlled analgesia, among others. It should be understood that the above describes only preferred embodiments of the invention. It should also be understood that while the preferred embodiments discuss gas sampling, such as CO₂ sampling and analysis, the concept of the invention includes sampling and analysis of other medical gases and vapors like propofol, oxygen, xenon and intravenous anesthetics. It should further be understood that although the preferred embodiments discussed address supplemental O₂ delivery, the concept of the invention is applicable to delivery of pure gases or mixtures of gases such as O₂/helium, O₂/air, and others.

What is claimed:

1. A method for supplying an inspired gas to a person while sampling expired gases from the person, the method comprising:

positioning an oronasal gas device on the person in an area between a nose and a mouth of the person, said oronasal device having a lumen for supplying a gas from a source to the person and fluid outlets that direct said supplied gas toward nostrils of the nose and toward the mouth for inhalation, said device also having portions that extend from a body of the device, two of said portions being nostril portions extending such that each may be inserted into a different nostril of the nose and a third portion extending into a breath stream of the mouth, said two nostril portions having fluid inlets adapted to channel expired gases from the nostrils to a sensor for detecting when said person is inhaling and exhaling, wherein said fluid outlets are located away from said fluid inlets to minimize mixing of expired gases and said supplied gas;

collecting expired gases using said fluid inlets and transmitting said collected expired gases through a plurality of lumens;

determining whether the person is in an exhalation or an inhalation phase of a respiratory cycle using said sensor;

delivering an increased flow of inspired gas to the person during the determined inhalation phase of the respiratory cycle; and analyzing said expired gases using an analyzer, said analyzer receiving expired gases collected by at least two of said fluid inlets independently via at least two of said lumens such that expired gases from said at least two fluid inlets are independently analyzed.

2. The method of claim 1, wherein the supplied gas includes pure gas.

3. The method of claim 2, wherein the pure gas includes oxygen.

4. The method of claim 1, wherein the inspired gas includes a gas mixture.

5. The method of claim 4, wherein the gas mixture includes a mixture of oxygen and air.

6. The method of claim 1, further comprising using said sensor to determine a primary respiratory site, and wherein said analyzer is adapted to analyze expired gases collected from said primary respiratory site.

7. The method of claim 6, wherein said determination of said primary respiratory site includes identifying a less obstructed one of said nostrils such that said analyzer is adapted to analyze expired gases collected from said less obstructed nostril by an appropriate one of said fluid inlets.

8. The method of claim 7, wherein the gas stream at the mouth is continuously sampled, in addition to sampling at said less obstructed one of said nostrils.

9. The method of claim 7, wherein said analyzing of said expired gases comprises monitoring the ventilation of the person at least in accordance with the determination of the person's primary respiratory site.

10. The method of claim 9, wherein an expired breath stream at the mouth is continuously collected and analyzed.

11. The method of claim 9, wherein the monitoring of the ventilation is accomplished by measuring the CO₂ levels in the person's expired breath gas stream.

12. The method of claim 11, wherein the monitoring of the ventilation is accomplished by measuring the end-tidal CO₂ value.

13. The method of claim 11, wherein the monitoring of the ventilation is accomplished by determining the area under the expired CO₂ time plot.

14. The method of claim 6, wherein determining said primary respiratory site is accomplished by sampling pressure at the respiratory sites and comparing said pressures to identify a respiratory site demonstrating a larger pressure swing.

15. The method of claim 1, wherein said determining of whether the person in the exhalation or inhalation phase comprises analyzing pressure in the person's breath gas streams collected in said fluid inlets with said sensor.

16. The method of claim 15, wherein said detector is a pressure transducer.

17. The method of claim 15, further comprising monitoring the respiratory rate in accord with the pressure analysis.

18. The method of claim 15, further comprising monitoring the inspiratory/expiratory time ratio in accord with the pressure analysis.

19. The method of claim 15, wherein the pressure in the person's breath gas stream is determined by sampling pressure at at least one respiratory site.

20. The method of claim 1, wherein the determining of whether the person is in the exhalation or inhalation phase comprises analyzing the humidity in the person's breath gas stream with said detecting lumens and said detector.

21. The method of claim 20, further comprising monitoring a respiratory rate in accord with the humidity analysis.

22. The method of claim 20, further comprising monitoring an inspiratory/expiratory time ratio in accord with the humidity analysis.

23. The method of claim 1, wherein the determining of whether the person is in the exhalation or inhalation phase comprises analyzing the temperature in the person's breath gas stream with said detecting lumens and said detector.

24. The method of claim 23, further comprising monitoring a respiratory rate in accord with the temperature analysis.

25. The method of claim 23, further comprising monitoring an inspiratory/expiratory time ratio in accord with the temperature analysis.

26. The method of claim 1, wherein analyzing said expired gases includes sampling the level of $CO_2$ in the person's expired breath gas stream.

27. The method of claim 1, further comprising delivering a decreased flow of inspired gas to the person during said exhalation phase, wherein said decreased flow is sufficiently low to avoid interfering with collecting of said expired gases.

28. The method of claim 1, wherein analyzing said expired gases comprises monitoring the level of a drug in the person's expired breath gas stream.

29. The method of claim 26, wherein the drug is an intravenous anesthetic.

30. The method of claim 26 wherein the drug is propofol.

31. The method of claim 1, wherein analyzing said expired gases comprises detecting xenon in the person's expired breath gas stream.

32. The method according to claim 1, wherein said lumens and said oronasal device comprise a pneumatic harness, and wherein said lumens are pre-packaged in one or more clusters, said clusters being manually separable from one another and thereby attachable to said oronasal device prior to positioning on the person.

33. The method according to claim 32, wherein said clusters have tear lines to permit separation of the lumens from one another.

34. The method according to claim 32, wherein each cluster has a cross section defining an aerofoil shape.

35. The method according to claim 32, wherein said pneumatic harness further comprises an adapter that facilitates connecting the pneumatic harness to a medical device.

36. The method according to claim 1, further comprising determining which of two nostrils of the nose is less obstructed, wherein said determining of the less obstructed nostril includes: sensing pressure in the gas stream of each nostril; comparing the pressure variations in the gas stream within each nostril; comparing the extent of variation of said pressures as between each nostril; and selecting the nostril with the larger pressure variation as the nostril that is less obstructed.

37. The method of claim 36, wherein the nostril that is less obstructed is selected to receive inspired gas.

38. The method of claim 36, wherein the nostril that is less obstructed is selected for said collecting of said expired gases.

39. The method of claim 1, wherein said portions each include a distal end and a proximate end, said distal ends having openings to said fluid inlets and said proximate ends being attached to a body of said cannula, and wherein said fluid outlets comprise a plurality of holes located immediately about and partially surrounding the proximate ends of said nostril portions.

40. The method of claim 39, wherein said fluid outlets comprise a plurality of holes arranged in an arc around a base of each nostril portion to diffuse supplied gas into each nostril respectively.

41. The method of claim 40, wherein said plurality of holes are arranged to deliver supplied gas toward said nostrils in a diffuse manner.

42. The method of claim 40, wherein said plurality of holes are arranged substantially concentrically to said nostril portions.

43. The method of claim 1, wherein said fluid outlets are located downstream from said fluid inlets relative to corresponding ones of said expired gases streams.

44. The method of claim 1, wherein said sensor is in communication with said nostril fluid inlets via sensor fluid channels running through said body, each said sensor fluid channel joining with a fluid inlet of one of said nostril portions.

45. The method of claim 44, wherein said analyzer is in communication with said nostril fluid inlets via analyzer fluid channels running through said body, at least one said analyzer fluid channel joining with a fluid inlet of each said nostril portion and one said analyzer channel joining with a fluid inlet of said third portion.

46. The method of claim 45, wherein said analyzer fluid channels connect said nostril fluid inlets to a first analyzer and said fluid inlet of said third prong to a second analyzer.

47. The method of claim 44, wherein said sensor detects pressure changes caused by expired gases exiting the nose.

48. The method of claim 1, wherein said delivery of said flow of inspired gas is performed by an automated gas delivery device, said delivery device comprising a flow control valve and a controller wherein the controller runs software that indicates an error to a user if while the flow control valve is open, the controller detects pressure at said source of said supplied gas but fails to detect pressure downstream of the flow control valve.

49. The method of claim 1, wherein said determining step comprises monitoring changes in a sum of the pressures detected at both nostrils.

50. The method of claim 49, wherein said delivering step comprises initiating said increased flow of inspired gas when said sum crosses an upper negative pressure threshold in a decreasing direction, and ceasing said increased flow when said sum crosses a lower negative pressure threshold in an increasing direction.

51. An apparatus that delivers inspired gas to a person and samples expired gases from the person, said apparatus comprising:

an inspired gas delivery device, said gas delivery device comprising a mechanism for delivering a variable flow of supplied gas for inspiration by the person and a controller for managing said mechanism in response to a determined phase of the person's respiration cycle;

a supply lumen for providing said supplied gas from said delivery device to the person;

a maskless oronasal device in fluid communication with said supply lumen, said oronasal device having an elongated body adapted to be situated on the person in an area between a nose and a mouth of the person, said oronasal device having portions adapted to extend from said body, two of said portions being nostril portions extending such that each may be inserted into a different nostril of the nose and a third portion extending into a breath stream of the mouth, and said oronasal device comprising a plurality of fluid outlets adapted to direct flow of supplied gas from said supply lumen in a direction of each nostril and a direction of the mouth for inhalation, wherein said portions each have fluid inlets adapted to collect expired gases individually from streams of expired gas emanating from each said nostril and said mouth;

a sensor in fluid communication with one or more of said two nostril fluid inlets of said oronasal device, said sensor generating signals to said controller indicating said determined breath phase of the person;

an analyzer adapted to detect characteristics of said expired breath gas streams, said analyzer being in electronic communication with said sensor and in fluid communication with two or more of said fluid inlets via a plurality of lumens, said analyzer thereby being adapted to detect characteristics of expired gases collected by at least two of said fluid inlets independently via at least two corresponding ones of said lumens; and wherein said analyzer detects said characteristics in coordination with the determined phase of the person's respiration cycle, and wherein the inspired gas delivery device controller modulates delivery of inspired gas to said oronasal device in accordance with the determined phase of the person's respiration cycle so as to provide a higher flow of supplied gas to the person during an inhalation phase.

52. The apparatus of claim 51, wherein said portions comprise at least one nasal portion for each said nostril and at least one portion for the mouth.

53. The apparatus of claim 52, wherein said sensor comprises a pressure comparator and wherein at least one of the inlets in two or more of said portions are connected to said pressure comparator such that said sensor can determine a primary respiratory site of the person.

54. The apparatus of claim 53, wherein said analyzer further comprises a gas detecting device wherein the gas detecting device comprises a nasal gas sampling device and an oral gas sampling device and wherein the controller selects at least the gas stream from the primary respiratory site for monitoring.

55. The apparatus of claim 51, wherein the controller directs said mechanism to deliver a higher flow of supplied gas during a portion of the inhalation phase of the person's respiratory cycle, and a lower flow of supplied gas otherwise.

56. The apparatus according to claim 55, wherein said portion of the inhalation phase ends in advance of the inhalation phase.

57. The apparatus of claim 51, wherein said analyzer further comprises a gas detecting device.

58. The apparatus of claim 57, wherein the gas detecting device is a capnometer.

59. The apparatus of claim 57, wherein said gas detecting device comprises a nasal gas sampling device and an oral gas sampling device, and wherein the oral and nasal gas sampling devices are capnometers in fluid communication with appropriate ones of said fluid inlets.

60. The apparatus of claim 51, wherein said inspired gas delivery device comprises a flow control valve and wherein the controller runs software that indicates an error to a user if while the flow control valve is open, the controller detects pressure at a source of said supplied gas but fails to detect pressure downstream of the flow control valve.

61. The apparatus of claim 51 also comprising an auditory breath sonification device that amplifies breath sounds.

62. The apparatus of claim 61, wherein the auditory breath sonification device is a microphone that amplifies actual breath sounds.

63. The apparatus of claim 51, further comprising an auditory breath sonification device, wherein the auditory breath sonification device comprises a white noise generator that provides simulated breath sounds in response to said determined phase.

64. The apparatus of claim 63, wherein said simulated breath sounds distinguish between inhalation and exhalation breath sounds according to said determined present phase of the person's respiration cycle.

65. The apparatus of claim 51, wherein the gas detecting device measures $CO_2$ presence.

66. The apparatus of claim 51, wherein the gas detecting device measures xenon presence.

67. The apparatus of claim 51, wherein the detector is adapted to identify traces of a drug in expired breath gas of the person.

68. The apparatus of claim 67, wherein the drug is an intravenous anesthetic.

69. The apparatus of claim 67, wherein the drug is propofol.

70. The apparatus of claim 51, wherein said portions have distal ends with openings for expired gas to enter said fluid inlets, and wherein said openings extend sufficiently into expired breath airstreams of one nostril of the nose or the mouth and away from said fluid outlets so as to limit interference by said supplied gas upon said analyzer.

71. The apparatus of claim 51, wherein the controller provides a reduced flow of supplied gas during an exhalation phase.

72. The apparatus of claim 51 wherein said lumens and said oronasal device are disposable, and wherein said lumens are packaged affixed to one another along separable tear lines.

73. The apparatus of claim 72, wherein the lumen that accommodates the flow of inspired gas is of larger circumference than the other lumens.

74. The apparatus according to claim 72, wherein said oronasal device is connected to an auditory device via a sound lumen, said auditory device creating a sound that is transmitted to the person such that said sound lumen functions as a stimulus channel that carries an auditory prompt to the person.

75. The apparatus according to claim 51, wherein said increased flow of supplied gas is delivered during a portion of the inhalation phase of the person's respiratory cycle, and wherein said portion of the inhalation phase ends in advance of the exhalation phase.

76. The apparatus according to claim 51, wherein said lumens and said oronasal device comprise a pneumatic harness, and wherein said lumens are pre-packaged in one or more clusters, said clusters being manually separable from one another and thereby attachable to said device body prior to positioning on the person.

77. The apparatus according to claim 76, wherein at least one of the lumens is larger than the other lumens.

78. The apparatus according to claim 76, wherein said clusters have tear lines to permit separation of the lumens from one another.

79. The apparatus according to claim 76, wherein at least one of said clusters has a cross section defining an aerofoil shape to accommodate multiple fluid communication channels.

80. The apparatus of claim 51, wherein said nostril portions include a distal end and a proximate end, said distal end having openings to said fluid inlets and said proximate ends being attached to said body, and wherein said fluid outlets comprise a plurality of holes located immediately about and partially surrounding the proximate end of each said nostril portion.

81. The apparatus of claim 80, wherein said fluid outlets comprise a plurality of holes arranged in an arc around a base of each nostril portion to diffuse supplied gas into each corresponding nostril.

82. The apparatus of claim 81, wherein said plurality of holes are arranged to deliver supplied gas toward said nostrils in a diffuse manner.

83. The apparatus of claim 81, wherein said plurality of holes are arranged in a pattern substantially concentrically to each nostril portion.

84. The apparatus of claim 51, wherein said fluid outlets are located downstream from said fluid inlets relative to corresponding ones of said expired gases streams.

85. The apparatus of claim 51, wherein said sensor is in communication with said nostril fluid inlets via sensor fluid channels running through said body, each said sensor fluid channel joining with a fluid inlet of one of said nostril portions.

86. The apparatus of claim 85, wherein said analyzer is in communication with said nostril fluid inlets via analyzer fluid channels running through said body, at least one said analyzer fluid channel joining with a fluid inlet of each said nostril portion and one said analyzer channel joining with a fluid inlet of said third portion.

87. The apparatus of claim 86, wherein said analyzer fluid channels connect said nostril fluid inlets to a first analyzer and said fluid inlet of said third portion to a second analyzer.

88. The apparatus of claim 85, wherein said sensor detects pressure changes caused by expired gases exiting the nose.

89. The apparatus of claim 51, wherein said sensor monitors changes in a sum of the pressures detected at both the nostrils.

90. The apparatus of claim 89, wherein said signal to said controller causes said controller to initiate said higher increased flow of inspired gas when said sum crosses an upper negative pressure threshold in a decreasing direction, and ceasing said higher flow when said sum crosses a lower negative pressure threshold in an increasing direction.

91. A method for delivering an inspired gas to a person and monitoring gases expired by the person, said method comprising:

determining the breath phase of the person with a detector, said detector having fluid lumens interfacing with the person via fluid inlets inserted in paths of one or more expired breath gas streams of the person, said paths emanating from nostrils napes of a nose and from a mouth of the patient, said fluid inlets being formed within portions of an oronasal device, said oronasal device having a body and said portions being attached at respective bases to said body and extending from said body, said fluid inlets being in fluid communication with said detector lumens through said body, and said determined breath phase including an inhalation phase and an exhalation phase;

delivering a relatively higher flow of an inspired gas to the person during the inhalation phase, said inspired gas being introduced proximate to the nose of the person via a plurality of fluid outlet holes in said device body, said holes being located immediately about the base of each said portion that extends toward said nostrils so as to partially surround each said portion that extend towards said nostrils; and monitoring gases in the one or more expired breath gas streams with an analyzer to assess the health of the person, said analyzer being in communication with one or more of said fluid inlets, and said analyzer thereby interfacing with the person via said one or more paths;

wherein said monitoring provides feedback for controlling flow of said inspired gas.

92. The method of claim 91 further comprising determining at least one of the breath rate and inspiratory/expiratory time ratio.

93. The method of claim 92, wherein determining at least one of the breath phase, breath rate and inspiratory/expiratory time ratio is accomplished by analyzing the pressure waveform produced within at least one of said paths during said phases.

94. The method of claim 92, wherein determining at least one of the breath phase, breath rate and inspiratory/expiratory time ratio is accomplished by monitoring the humidity at at least one respiratory site.

95. The method of claim 92, wherein determining at least one of the breath phase, breath rate and inspiratory/expiratory time ratio is accomplished by monitoring the temperature at at least one respiratory site.

96. The method of claim 91 also comprising the step of delivering a relatively lower flow of inspired gas during the exhalation phase.

97. The method of claim 91, wherein the monitoring of exhaled gas is performed during a period of lower gas flow in the exhalation phase.

98. The method of claim 91, wherein said nostril portions include a distal end and a proximate end, said distal end having openings to said fluid inlets and said proximate ends being attached to said body of said oronasal device, and wherein said fluid outlet holes are located immediately about and partially surrounding the proximate end of said nostril portions.

99. The method of claim 98, wherein said fluid outlet holes are arranged in an arc around the base of each nostril portion to diffuse supplied gas into each nostril.

100. The method of claim 99, wherein said plurality of holes are arranged to deliver supplied gas into said nostrils in a diffuse manner.

101. The method of claim 99, wherein said plurality of holes are arranged in a substantially concentric pattern around each said nostril portion.

102. The method of claim 91, wherein said fluid outlet holes are located downstream from said fluid inlets relative to corresponding ones of said expired streams.

103. The method of claim 91, wherein said sensor is in communication with said nostril fluid inlets via sensor fluid channels running through said body, each said sensor fluid channel joining with a fluid inlet of one of said nostril portions.

104. The method of claim 103, wherein said analyzer is in communication with said nostril fluid inlets via analyzer fluid channels running through said body, at least one said analyzer fluid channel joining with a fluid inlet of each said nostril portion and one said analyzer fluid channel joining with a fluid inlet of said third portion.

105. The method of claim 104, wherein said analyzer fluid channels connect said nostril portion fluid inlets to a first analyzer and said third portion fluid inlets to a second analyzer, and said monitoring step utilizes said first and said second analyzer in cooperation.

106. The method of claim 103, wherein said sensor detects pressure changes caused by expired gases exiting the nose.

107. The method of claim 91, wherein said delivery of said flow of inspired gas is performed by an automated gas delivery device, said delivery device comprising a flow control valve and a controller wherein the controller runs software that indicates an error to a user if while the flow control valve is open, the controller detects pressure at said source of said supplied gas but fails to detect pressure downstream of the flow control valve.

108. The method of claim 91, wherein said determining step comprises monitoring changes in a sum of the pressures detected at both the nostrils.

109. The method of claim 108, wherein said delivering step comprises initiating said relatively higher flow of inspired gas when said sum crosses an upper negative pressure threshold in a decreasing direction, and ceasing said relatively higher flow when said sum crosses a lower negative pressure threshold in an increasing direction.

110. An apparatus that delivers inspired gas to a person and samples expired gases from the person, said apparatus comprising:
an inspired gas delivery device, said gas delivery device comprising a mechanism for delivering a variable flow of supplied gas for inspiration by the person and a controller for managing said mechanism in response to a determined phase of the person's respiration cycle;
a supply lumen for providing said supplied gas from said delivery device to the person;
a maskless oronasal device in fluid communication with said supply lumen, said oronasal device having an elongated body adapted to be situated on the person in an area between a nose and a mouth of the person, said oronasal device having portions adapted to extend from said body, two of said portions being nostril portions extending such that each may be inserted into a different nostril of the nose and a third portion extending into a breath stream of the mouth, and said oronasal device comprising a plurality of fluid outlets adapted to direct flow of supplied gas from said supply lumen in a direction of each nostril and a direction of the mouth for inhalation, wherein said portions each have fluid inlets adapted to collect expired gases individually from streams of expired gas emanating from each said nostril and said mouth;
a sensor in fluid communication with said two nostril fluid inlets of said oronasal device, said sensor generating signals to said controller indicating said determined breath phase of the person;
an analyzer system in fluid communication with said fluid inlets and adapted to detect characteristics of said expired breath gas streams, said analyzer system comprising one or more analyzer devices being in electronic communication with said sensor; and said fluid communication of said analyzer system with said fluid inlets comprising multiple lumens that allow fluid communication with said fluid inlet of said third portion to be independent of fluid communication of said analyzer system with at least one of said fluid inlets of said nostril portions; and
wherein said analyzer system detects said characteristics in coordination with the determined phase of the person's respiration cycle, and wherein the inspired gas delivery device controller modulates delivery of inspired gas to said oronasal device in accordance with the determined phase of the person's respiration cycle so as to provide a higher flow of supplied gas to the person during an inhalation phase and a lower flow of supplied gas to the person during an exhalation phase.

111. The apparatus of claim 110, wherein said analyzer devices comprise capnographs.

112. The apparatus of claim 110, wherein said wherein said nostril portions include a distal end and a proximate end, said distal end having openings to said fluid inlets and said proximate ends being attached to said body of said oronasal device, and wherein said fluid outlet holes are located immediately about and partially surrounding the proximate end of each said nostril portion.

113. The apparatus of claim 112, wherein said fluid outlet holes are arranged in a concentric arc around the base of each nostril portion to diffuse supplied gas into each nostril.

* * * * *